(12) United States Patent
Nabika et al.

(10) Patent No.: US 6,548,686 B2
(45) Date of Patent: Apr. 15, 2003

(54) TRANSITION METAL COMPOUND, CATALYST FOR ADDITION POLYMERIZATION, AND PROCESS FOR PRODUCING ADDITION POLYMER

(75) Inventors: Masaaki Nabika, Ichihara (JP); Tatsuya Miyatake, Ichihara (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/883,331

(22) Filed: Jun. 19, 2001

(65) Prior Publication Data

US 2002/0013433 A1 Jan. 31, 2002

(30) Foreign Application Priority Data

Jun. 21, 2000 (JP) ......................................... 2000-185962

(51) Int. Cl.⁷ ................................................. C07F 7/00
(52) U.S. Cl. ............................ 556/51; 556/11; 556/12; 556/52
(58) Field of Search .................. 556/11, 51, 10, 556/52

(56) References Cited

U.S. PATENT DOCUMENTS

| | | | |
|---|---|---|---|
| 4,542,199 A | 9/1985 | Kaminsky et al. | 526/160 |
| 5,532,394 A | 7/1996 | Rosen et al. | 556/11 |
| 5,986,029 A | * 11/1999 | van Beek et al. | 526/160 |
| 6,329,478 B1 | * 12/2001 | Katayama et al. | 526/127 |
| 2002/0013433 A1 | * 1/2002 | Nabika et al. | 526/110 |

FOREIGN PATENT DOCUMENTS

| | | | |
|---|---|---|---|
| EP | 416 815 A2 | * 3/1991 | ........... C08F/10/00 |
| EP | 0 887 355 A1 | 12/1998 | |
| EP | 0 963 990 A1 | 12/1999 | |
| JP | 9-77818 A2 | * 3/1997 | |
| WO | WO 92/12112 | 7/1992 | |
| WO | WO 92/12117 | 7/1992 | |
| WO | WO 96/13529 | 5/1996 | |

OTHER PUBLICATIONS

Huang, Q.; Qian, Y.; Li, G. Transition Met. Chem. 1990, 15, 483.*
Chen, Y.–X.; Fu, P–F.; Stern, C. L. Marks, T. J. Organometallics 1997, 16, 5958.*
Rau, A.; Schmitz, S.; Luft, G. J. Organomet. Chem. 2000, 608, 71 (abstract).*
Tian et al., J. Organomet. Chem., vol. 558, pp. 231–233, (1998).
Rau et al., J. Organomet. Chem., vol. 608, pp. 71–75, (2000).

* cited by examiner

Primary Examiner—David W. Wu
Assistant Examiner—Rip A. Lee
(74) Attorney, Agent, or Firm—Birch, Stewart, Kolasch & Birch, LLP (57) ABSTRACT

A transition metal compound represented by the general formula (3):

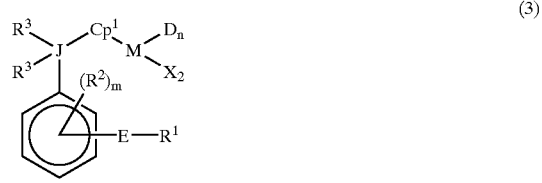

(3)

wherein M represents a titanium atom, zirconium atom or hafnium atom in the +3 oxidation state; $Cp^1$ represents a group having a cyclopentadiene-containing anion skeleton; J represents an atom of XIV group in the periodic table of element; each of $R^2$ and $R^3$ independently represents a hydrogen atom, halogen atom, alkyl group, aralkyl group, aryl group, substituted silyl group, alkoxy group, aralkyloxy group, aryloxy group or di-substituted amino group, and a plurality of $R^2$s may bond mutually to form a ring; m represents an integer of from 0 to 4; E represents an oxygen atom or sulfur atom; $R^1$ represents an alkyl group, aralkyl group, aryl group or substituted silyl group; each of two Xs independently represents a hydrogen atom, halogen atom, alkyl group, aralkyl group, aryl group, substituted silyl group, alkoxy group, aralkyloxy group, aryloxy group or di-substituted amino group, and two Xs may bond mutually to form a ring; D represents a neutral ligand coordinated on M; and n represents an integer of from 0 to 2.

5 Claims, 1 Drawing Sheet

Fig. 1

TRANSITION METAL COMPOUND, CATALYST FOR ADDITION POLYMERIZATION, AND PROCESS FOR PRODUCING ADDITION POLYMER

BACKGROUND OF THE INVENTION

1. Field of the Invention

The present invention relates to a transition metal compound having a multidentate mono-anionic ligand containing a hetero atom as a substituent, a catalyst for addition polymerization obtained by using said transition metal compound, and a process for producing an addition polymer with the catalyst.

2. Description of Related Arts

Regarding a method for producing an addition polymer with a single site catalyst composed of a metallocene complex or the like, many reports have done. For example, JP-A-58-19309 discloses a method for producing an olefin polymer with a metallocene complex and an aluminoxane. There has been a problem that when addition polymerization of an olefin or the like is conducted in such a system, the amount of the initial heat generation is large particularly due to high initial activity and consequently control of the polymerization reaction is difficult.

SUMMARY OF THE INVENTION

Under the above-situation, an object of the present invention is to provide a transition metal compound useful for preparing a catalyst for addition polymerization having a catalytic activity which suppresses heat generation at the beginning of polymerization and can be industrially carried out, and such a catalyst for addition polymerization, and an efficient process for producing an addition polymer, which can suppress heat generation at the beginning of polymerization and can be industrially carried out.

Namely, the present invention relates to a transition metal compound (A) of the following general formula (1):

(1)

(wherein, M represents a titanium atom, zirconium atom or hafnium atom in the +3 formal oxide condition; A represents a multidentate mono-anionic ligand; $R^1$ represents an alkyl group, aralkyl group, aryl group or substituted silyl group; E represents an oxygen atom or sulfur atom; each of two Xs independently represents a hydrogen atom, halogen atom, alkyl group, aralkyl group, aryl group, substituted silyl group, alkoxy group, aralkyloxy group, aryloxy group or di-substituted amino group, and two Xs may bond mutually to form a ring; D represents a neutral ligand coordinated on M; and n represents an integer of from 0 to 2.).

Further, the present invention relates to a catalyst for addition polymerization obtained by bringing the transition metal compound (A) into contact with the following (B) and/or (C):

(B) one or more aluminum compounds selected from the following (B1) to (B3);
  (B1) organic aluminum compounds of the general formula $E^1{}_a AlZ_{3-a}$,
  (B2) cyclic aluminoxanes having a structure of the general formula $\{-Al(E^2)-O-\}_b$, and
  (B3) linear aluminoxanes having a structure of the general formula $E^3 \{-Al(E^3)-O-\}_c AlE^3{}_2$ (wherein, each of $E^1$, $E^2$ and $E^3$ represents a hydrocarbon group, and all $E^1$ s, all $E^2$ s or all $E^3$ s may be the same or different. Z represents a hydrogen atom or halogen atom, and all Zs may be the same or different a represents a number satisfying $0 < a \leqq 3$, b represents an integer of 2 or more, and c represents an integer of 1 or more.), (C) one or more boron compounds selected from the following (C1) to (C3):
  (C1) boron compounds of the general formula $BQ^1 Q^2 Q^3$,
  (C2) boron compounds of the general formula $G^+(BQ^1 Q^2 Q^3 Q^4)^-$, and
  (C3) boron compounds of the general formula $(L-H)^+ (BQ^1 Q^2 Q^3 Q^4)^-$
(wherein, B represents a trivalent boron atom, and $Q^1$ to $Q^4$ represent a halogen atom, hydrocarbon group, halogenated hydrocarbon group, substituted silyl group, alkoxy group or di-substituted amino group, and they may be the same or different. $G^+$ represents an inorganic or organic cation, and L represents a neutral Lewis base and $(L-H)^+$ represents a Brønsted acid.).

DETAILED DESCRIPTION OF THE INVENTION

Figure 1:
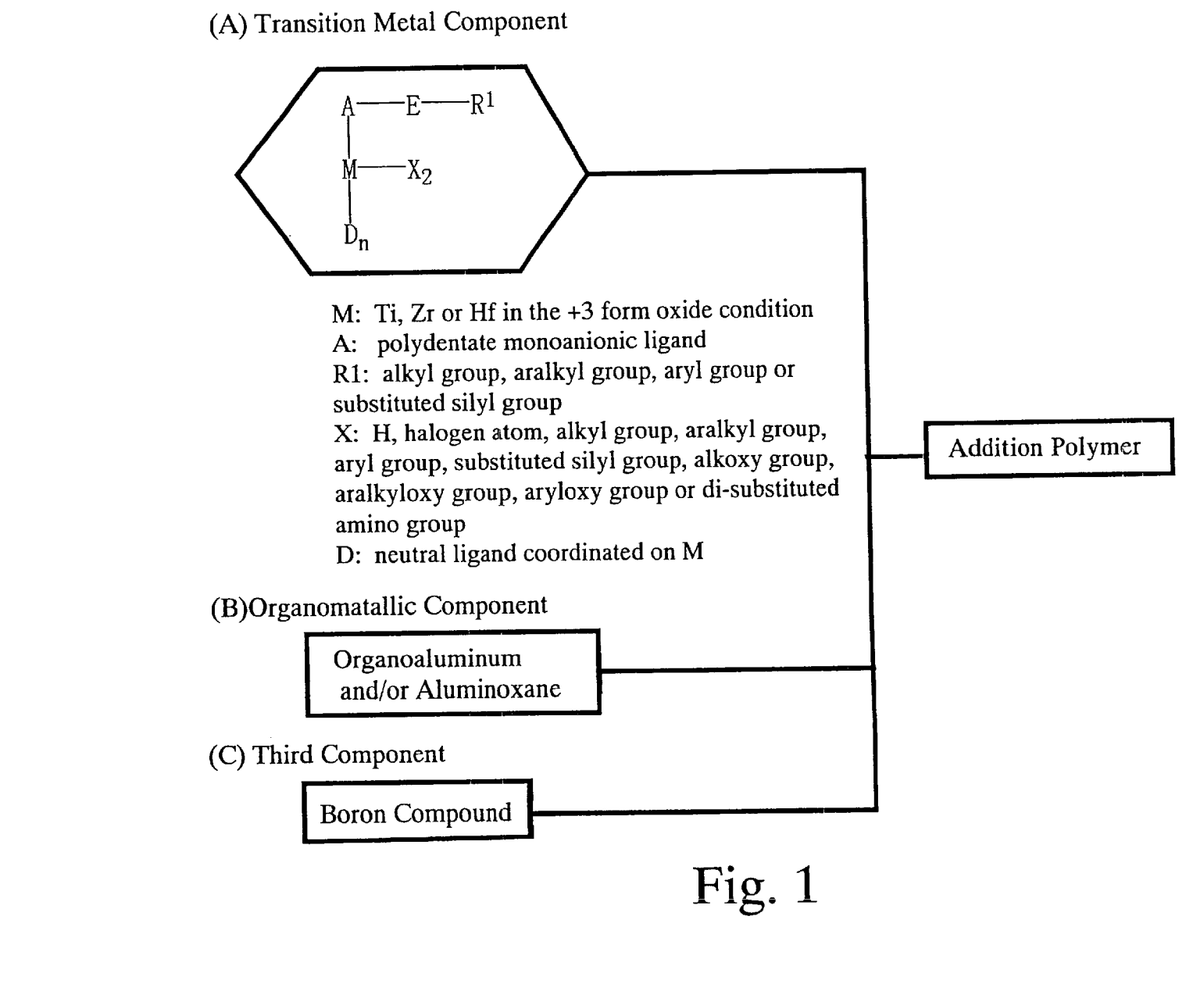
FIG. 1 is a flow chart for assisting understanding of the present invention. This flowchart shows atypical example of embodiments of the present invention, and the scope of the present invention is not limited at all thereto.

The present invention will be illustrated in detail below.

In the transition metal compound (A) of the above-mentioned general formula (1), M represents a titanium atom, zirconium atom or hafnium atom in the +3 formal oxidation state, and particularly preferably a titanium atom in the +3 formal oxidation state.

Examples of the neutral ligand represented by D coordinated on M, in the general formula (1), include, for example, ether compounds such as diethyl ether, tetrahydrofuran, di-n-butyl ether, di-iso-butyl ether, di-tert-butyl ether and the like, tertiary amine compounds such as triethylamine, pyridine and the like, nitrile compounds such as acetonitrile, benzonitrile and the like, etc., and preferably tetrahydrofuran and pyridine.

E in the general formula (1) is an oxygen atom or sulfur atom, and preferably an oxygen atom.

As the halogen atom represented by X in the general formula (1), a fluorine atom, chlorine atom, bromine atom, iodine atom and the like are exemplified, and particularly preferable is a chlorine atom.

As the alkyl group represented by X or $R^1$ in the general formula (1), an alkyl group having 1 to 20 carbon atoms is preferable, and examples thereof include a methyl group, ethyl group, n-propyl group, isopropyl group, n-butyl group, sec-butyl group, tert-butyl group, isobutyl group, n-pentyl group, neopentyl group, amyl group, n-hexyl group, n-octyl group, n-decyl group, n-dodecyl group, n-pentadecyl group, n-eicosyl group and the like, and more preferable examples are a methyl group, ethyl group, isopropyl group, tert-butyl group, isobutyl group and amyl group.

Any of these alkyl groups may be substituted with a halogen atom such as a fluorine atom, chlorine atom, bromine atom, iodine atom and the like. Examples of the alkyl group having 1 to 10 carbon atoms substituted with a halogen atom include a fluoromethyl group, difluoromethyl group, trifluoromethyl group, chloromethyl group, dichloromethyl group, trichloromethyl group, bromomethyl group, dibromomethyl group, tribromomethyl group, iodomethyl group, diiodomethyl group, triiodomethyl group, fluoroethyl group, difluoroethyl group, trifluoroethyl group, tetrafluoroethyl group, pentafluoroethyl group, chloroethyl group, dichloroethyl group, trichloroethyl group, tetrachloroethyl group, pentachloroethyl group, bromoethyl group, dibromoethyl group, tribromoethyl group, tetrabromoethyl group, pentabromoethyl group, perfluoropropyl group, perfluorobutyl group, perfluoropentyl group, perfluorohexyl group, perfluorooctyl group, perfluorododecyl group, perfluoropentadecyl group, perfluoroeicosyl group, perchloropropyl group, perchlorobutyl group, perchloropentyl group, perchlorohexyl group, perchlorooctyl group, perchlorododecyl group, perchloropentadecyl group, perchloroeicosyl group, perbromopropyl group, perbromobutyl group, perbromopentyl group, perbromohexyl group, perbromooctyl group, perbromododecyl group, perbromopentadecyl group, perbromoeicosyl group and the like.

Further, any of these alkyl groups may also be partially substituted with an alkoxy group such as a methoxy group, ethoxy group and the like, an aryloxy group such as a phenoxy group and the like, an aralkyloxy group such as a benzyloxy group and the like, etc.

As the aralkyl group represented by X or $R^1$ in the above-mentioned general formula (1), an aralkyl group having 7 to 20 carbon atoms is preferable, and examples thereof include a benzyl group, (2-methylphenyl)methyl group, (3-methylphenyl)methyl group, (4-methylphenyl) methyl group, (2, 3-dimethylphenyl)methyl group, (2, 4-dimethylphenyl)methyl group, (2, 5-dimethylphenyl) methyl group, (2, 6-dimethylphenyl)methyl group, (3, 4-dimethylphenyl)methyl group, (3, 5-dimethylphenyl) methyl group, (2, 3, 4-trimethylphenyl)methyl group, (2, 3, 5-trimethylphenyl)methyl group, (2, 3, 6-trimethylphenyl) methyl group, (3, 4, 5-trimethylphenyl)methyl group, (2, 4, 6-trimethylphenyl)methyl group, (2, 3, 4, 5-tetramethylphenyl)methyl group, (2, 3, 4, 6-tetramethylphenyl)methyl group, (2, 3, 5, 6-tetramethylphenyl)methyl group, (pentamethylphenyl) methyl group, (ethylphenyl)methyl group, (n-propylphenyl) methyl group, (isopropylphenyl)methyl group, (n-butylphenyl)methyl group, (sec-butylphenyl)methyl group, (tert-butylphenyl)methyl group, (n-pentylphenyl) methyl group, (neopentylphenyl)methyl group, (n-hexylphenyl)methyl group, (n-octylphenyl)methyl group, (n-decylphenyl)methyl group, (n-dodecylphenyl)methyl group, naphthylmethyl group, anthracenylmethyl group and the like, and a benzyl group is preferable.

Any of these aralkyl groups may also be partially substituted with a halogen atom such as a fluorine atom, chlorine atom, bromine atom, iodine atom and the like, an alkoxy group such as a methoxy group, ethoxy group and the like, an aryloxy group such as a phenoxy group and the like, an aralkyloxy group such as a benzyloxy group and the like, etc.

As the aryl group represented by X or $R^1$ in the general formula (1), an aryl group having 6 to 20 carbon atoms is preferable, and examples thereof include a phenyl group, 2-tolyl group, 3-tolyl group, 4-tolyl group, 2, 3-xylyl group, 2, 4-xylyl group, 2, 5-xylyl group, 2, 6-xylyl group, 3, 4-xylyl group, 3, 5-xylyl group, 2, 3, 4-trimethylphenyl group, 2, 3, 5-trimethylphenyl group, 2, 3, 6-trimethylphenyl group, 2, 4, 6-trimethylphenyl group, 3, 4, 5-trimethylphenyl group, 2, 3, 4, 5-tetramethylphenyl group, 2, 3, 4, 6-tetramethylphenyl group, 2, 3, 5, 6-tetramethylphenyl group, pentamethylphenyl group, ethylphenyl group, n-propylphenyl group, isopropylphenyl group, n-butylphenyl group, sec-butylphenyl group, tert-butylphenyl group, di-tert-butylphenyl group, di-tert-butylmethylphenyl group, n-pentylphenyl group, neopentylphenyl group, n-hexylphenyl group, n-octylphenyl group, n-decylphenyl group, n-dodecylphenyl group, n-tetradecylphenyl group, naphthyl group, anthracenyl group and the like, and a phenyl group is more preferable.

Any of these aryl groups may also be partially substituted with a halogen atom such as a fluorine atom, chlorine atom, bromine atom, iodine atom and the like, an alkoxy group such as a methoxy group, ethoxy group and the like, an aryloxy group such as a phenoxy group and the like, an aralkyloxy group such as a benzyloxy group and the like, etc.

As the substituted silyl group represented by X or $R^1$ in the general formula (1), a silyl group substituted with a hydrocarbon group is preferable, and examples of the hydrocarbon group include alkyl groups having 1 to 10 carbon atoms such as a methyl group, ethyl group, n-propyl group, isopropyl group, n-butyl group, sec-butyl group, tert-butyl group, isobutyl group, n-pentyl group, n-hexyl group, cyclohexyl group and the like, and aryl groups such as a phenyl group and the like, etc. As such substituted silyl group having 1 to 20 carbon atoms, for example, mono-substituted silyl groups having 1 to 20 carbon atoms such as a methylsilyl group, ethylsilyl group, phenylsilyl group and the like, di-substituted silyl groups having 2 to 20 carbon atoms such as a dimethylsilyl group, diethylsilyl group, diphenylsilyl group and the like, tri-substituted silyl groups having 3 to 20 carbon atoms such as a trimethylsilyl group, triethylsilyl group, tri-n-propylsilyl group, triisopropylsilyl group, tri-n-butylsilyl group, tri-sec-butylsilyl group, tri-tert-butylsilyl group, triisobutylsilyl group, tert-butyldimethylsilyl group, tri-n-pentylsilyl group, tri-n-hexylsilyl group, tricyclohexylsilyl group, triphenylsilyl group and the like, etc. are listed, and preferable are a trimethylsilyl group, tert-butyldimethylsilyl group and triphenylsilyl group.

Any of these substituted silyl groups may also be partially substituted with a halogen atom such as a fluorine atom, chlorine atom, bromine atom, iodine atom and the like, an alkoxy group such as a methoxy group, ethoxy group and the like, an aryloxy group such as a phenoxy group and the like, an aralkyloxy group such as a benzyloxy group and the like, etc.

As the alkoxy group represented by X in the general formula (1), an alkoxy group having 1 to 20 carbon atoms is preferable, and examples thereof include a methoxy group, ethoxy group, n-propoxy group, isopropoxy group, n-butoxy group, sec-butoxy group, tert-butoxy group, n-pentoxy group, neopentoxy group, n-hexoxy group, n-octoxy group, n-dodecoxy group, n-pentadecoxy group, n-icoxoxy group and the like, and more preferable are a methoxy group, ethoxy group, isopropoxy group and tert-butoxy group.

Any of these alkoxy groups may also be partially substituted with a halogen atom such as a fluorine atom, chlorine atom, bromine atom, iodine atom and the like, an alkoxy group such as a methoxy group, ethoxy group and the like, an aryloxy group such as a phenoxy group and the like, an aralkyloxy group such as a benzyloxy group and the like, etc.

As the aralkyloxy group represented by X in the general formula (1), an aralkyloxy group having 7 to 20 carbon atoms is preferable, and examples thereof include a benzyloxy group, (2-methylphenyl)methoxy group, (3-methylphenyl)methoxy group, (4-methylphenyl)methoxy group, (2, 3-dimethylphenyl)methoxy group, (2, 4-dimethylphenyl)methoxy group, (2, 5-dimethylphenyl) methoxy group, (2, 6-dimethylphenyl)methoxy group, (3, 4-dimethylphenyl)methoxy group, (3, 5-dimethylphenyl) methoxy group, (2, 3, 4-trimethylphenyl)methoxy group, (2, 3, 5-trimethylphenyl)methoxy group, (2, 3, 6-trimethylphenyl)methoxy group, (2, 4, 5-trimethylphenyl) methoxy group, (2, 4, 6-trimethylphenyl)methoxy group, (3, 4, 5-trimethylphenyl)methoxy group, (2, 3, 4, 5-tetramethylphenyl)methoxy group, (2, 3, 4, 6-tetiamethylphenyl)methoxy group, (2, 3, 5, 6-tetramethylphenyl)methoxy group, (pentamethylphenyl) methoxy group, (ethylphenyl)methoxy group, (n-propylphenyl)methoxy group, (isopropylphenyl)methoxy group, (n-butylphenyl)methoxy group, (sec-butylphenyl) methoxy group, (tert-butylphenyl)methoxy group, (n-hexylphenyl)methoxy group, (n-octylphenyl)methoxy group, (n-decylphenyl)methoxy group, naphthylmethoxy group, anthracenylmethoxy group and the like, and more preferable is a benzyloxy group.

Any of these aralkyloxy groups may also be partially substituted with a halogen atom such as a fluorine atom, chlorine atom, bromine atom, iodine atom and the like, an alkoxy group such as a methoxy group, ethoxy group and the like, an aryloxy group such as a phenoxy group and the like, an aralkyloxy group such as a benzyloxy group and the like, etc.

As the aryloxy group represented by X in the general formula (1), an aryloxy group having 6 to 20 carbon atoms is preferable, and examples thereof include a phenoxy group, 2-methylphenoxy group, 3-methylphenoxy group, 4-methylphenoxy group, 2, 3-dimethylphenoxy group, 2, 4-dimethylphenoxy group, 2, 5-dimethylphenoxy group, 2, 6-dimethylphenoxy group, 3, 4-dimethylphenoxy group, 3, 5-dimethylphenoxy group, 2-tert-butyl-3-methylphenoxy group, 2-tert-butyl-4-methylphenoxy group, 2-tert-butyl-5-methylphenoxy group, 2-tert-butyl-6-methylphenoxy group, 2, 3, 4-trimethylphenoxy group, 2, 3, 5-trimethylphenoxygroup, 2, 3, 6-trimethylphenoxy group, 2, 4, 5-trimethylphenoxygroup, 2, 4, 6-trimethylphenoxy group, 2-tert-butyl-3, 4-dimethylphenoxy group, 2-tert-butyl-3, 5-dimethylphenoxy group, 2- tert-butyl- 3, 6- dimethylphenoxy group, 2, 6-di-tert-butyl-3-methylphenoxy group, 2-tert-butyl-4, 5-dimethylphenoxy group, 2, 6-di-tert-butyl-4-methylphenoxy group, 3, 4, 5-trimethylphenoxy group, 2, 3, 4, 5-tetramethylphenoxy group , 2-tert-butyl-3, 4, 5-trimethylphenoxy group, 2, 3, 4, 6-tetramethylphenoxy group, 2-tert-butyl-3, 4, 6-trimethylphenoxy group, 2, 6-di-tert-butyl-3, 4-dimethylphenoxy group, 2, 3, 5, 6-tetramethylphenoxy group, 2-tert-butyl-3, 5, 6-trimethylphenoxy group, 2, 6-di-tert-butyl-3, 5-dimethylphenoxy group, pentamethylphenoxy group, ethylphenoxy group, n-propylphenoxy group, isopropylphenoxy group, n-butylphenoxy group, sec-butylphenyl group, tert-butylphenoxy group, n-hexylphenoxy group, n-octylphenoxy group, n-decylphenoxy group, n-tetradecylphenoxy group, naphthoxy group, anthracenoxy group and the like.

Any of these aryloxy groups may also be partially substituted with a halogen atom such as a fluorine atom, chlorine atom, bromine atom, iodine atom and the like, an alkoxy group such as a methoxy group, ethoxy group and the like, an aryloxy group such as a phenoxy group and the like, an aralkyloxy group such as a benzyloxy group and the like, etc.

As the di-substituted amino group represented by X in the general formula (1), an amino group substituted with two hydrocarbon groups or silyl groups is preferable, and examples of the hydrocarbon group include alkyl groups having1 to 10 carbon atoms such as a methyl group, ethyl group, n-propyl group, isopropyl group, n-butyl group, sec-butyl group, tert-butyl group, isobutyl group, n-pentyl group, n-hexyl group, cyclohexyl group and the like, aryl groups having 6 to 10 carbon atoms such as a phenyl group and the like, and aralkyl groups having 7 to 10 carbon atoms such as a benzyl group and the like, etc. and examples of the silyl group include a trimethylsilyl group, tert-butyldimethylsilyl group and the like. Examples of such di-substituted amino group include a dimethylamino group, diethylamino group, di-n-propylamino group, diisopropylamino group, di-n-butylamino group, di-sec-butylamino group, di-tert-butylamino group, diiosobutylamino group, tert-butylisopropylamino group, di-n-hexylamino group, di-n-octylamino group, diphenylamino group, bistrimethylsilylamino group, bis-tert-butyldimethylsilylamino group and the like, and preferable are a dimethylamino group, diethylamino group, diisopropylamino group, di-tert-butylamino group and bistrimethylsilylamino group.

Any of these di-substituted amino groups may also be partially substituted with a halogen atom such as a fluorine atom, chlorine atom, bromine atom, iodine atom and the like, an alkoxy group such as a methoxy group, ethoxy group and the like, an aryloxy group such as a phenoxy group and the like, an aralkyloxy group such as a benzyloxy group and the like, etc.

$R^1$ in the general formula (1) is preferably the alkyl group or substituted silyl group, and a methyl group, tert-butyl group or trimethylsilyl group is more preferable.

Two Xs in the general formula (1) may mutually bond to form a ring. As X, the halogen atom, alkyl group, alkoxy group or alkenediyl group is preferable, and a chlorine atom, methyl group, methoxy group, 3-hexene-2, 5-diyl group or 1, 4-diphenyl-2-butene-1, 4-diyl group is further preferable.

As the multidentate mono-anionic ligand represented by A in the general formula (1), for example, a cyclopentadienyl group, substituted cyclopentadienyl group, indenyl group, substituted indenyl group, fluorenyl group, substituted fluorenyl group, tris(pyrazolyl) borate group, tris(substituted pyrazolyl) borate group and the like are listed, and preferable are a substituted cyclopentadienyl group, substituted indenyl group and.substituted fluorenyl group.

A is preferably a multidentate mono-anionic ligand of the following general formula (2):

$$—Cp^1—G— \quad (2)$$

wherein $Cp^1$ represents a group having a cyclopentadiene type anion skeleton; and G represents a substituent having 1 to 30 non-hydrogen atoms binding between $Cp^1$ and E.

As the group having a cyclopentadiene-type anion skeleton represented by $Cp^1$ in the above-mentioned general formula (2), there are listed, for example, an $\eta^5$-cyclopentadienyl group, $\eta^5$-methylcyclopentadienyl group, η⁵-dimethylcyclopentadienyl group, η⁵-trimethylcyclopentadienyl group, η⁵-tetramethylcyclopentadienyl group, η⁵-ethylcyclopentadienyl group, η⁵-n-propylcyclopentadienyl group, η⁵-isopropylcyclopentadienyl group, η⁵-n-butylcyclopentadienyl group, η⁵-sec-butylcyclopentadienyl group, η⁵-tert-butylcyclopentadienyl group, η⁵-n-pentylcyclopentadienyl group, η⁵-neopentylcyclopentadienyl group, η⁵-n-hexylcyclopentadienyl group, η⁵-n-octylcyclopentadienyl group, η⁵-phenylcyclopentadienyl group, η⁵-naphthylcyclopentadienyl group, η⁵-trimethylsilylcyclopentadienyl group, η⁵-triethylsilylcyclopentadienyl group, η⁵-tert-butyldimethylsilylcyclopentadienyl group, η⁵-indenyl group, η⁵-methylindenyl group, η⁵-dimethylindenyl group, η⁵-ethylindenyl group, η⁵-n-propylindenyl group, η⁵-isopropylindenyl group, η⁵-n-butylindenyl group, η⁵-sec-butylindenyl group, η⁵-tert-butylindenyl group, η⁵-n-pentylindenyl group, η⁵-neopentylindenyl group, η⁵-n-hexylindenyl group, η⁵-n-octylindenyl group, η⁵-n-decylindenyl group, η⁵-phenylindenyl group, η⁵-methylphenylindenyl group, η⁵-naphthylindenyl group, η⁵-trimethylsilylindenyl group, η⁵-triethylsilylindenyl group, η⁵-tert-butyldimethylsilylindenyl group, η⁵-tetrahydroindenyl group, η⁵-fluorenyl group, η⁵-methylfluorenyl group, η⁵-dimethylfluorenyl group, η⁵-ethylfluorenyl group, η⁵-diethylfluorenyl group, η⁵-n-propylfluorenylgroup, η⁵-di-n-propylfluorenylgroup, η⁵-isopropylfluorenyl group, η⁵-diisopropylfluorenyl group, η⁵-n-butylfluorenyl group, η⁵-sec-butylfluorenyl group, η⁵-tert-butylfluorenyl group, η⁵-di-n-butylfluorenyl group, η⁵-di-sec-butylfluorenyl group, η⁵-di-tert-butylfluorenyl group, η⁵-n-pentylfluorenyl group, η⁵-neopentylfluorenyl group, η⁵-n-hexylfluorenylgroup, η⁵-n-octylfluorenylgroup, η⁵-n-decylfluorenyl group, η⁵-n-dodecylfluorenyl group, η⁵-phenylfluorenyl group, η⁵-di-phenylfluorenyl group, η⁵-methylphenylfluorenyl group, η⁵-naphthylfluorenyl group, η⁵-trimethylsilylfluorenyl group, η⁵-bis-trimethylsilylfluorenyl group, η⁵-triethylsilylfluorenyl group, η⁵-tert-butyldimethylsilylfluorenyl group and the like, and preferable are a η⁵-cyclopentadienyl group, η⁵-methylcyclopentadienyl group, η⁵-tert-butylcyclopentadienyl group, η⁵-tetramethylcyclopentadienyl group, η⁵-indenyl group and ⁵-fluorenyl group.

G in the general formula (2) represents a substituent having 1 to 30 non-hydrogen atoms binding $Cp^1$ with E, and examples thereof include a methylene group; polymethylene groups such as a 1, 2-ethylene group, 1, 3-propylene group and the like; cycloalkanediyl group; silicon-containing hydrocarbon groups such as a dialkylsilylene group, silacycloalkanedilyl group and the like; germanium-containing hydrocarbon groups such as a dialkylgermylene group, germylacycloalkanediyl group and the like; atoms of XVI group in the periodic table such as an oxygen atom and sulfur atom; substituted phenylene and the like, and in some cases, a substituent combining them may also be permissible, and preferable are a polymethylene group, substituted phenylene group, substituted phenyleneoxy group, substituted phenylenethio group and groups of the following general formula (4), and particularly preferable are groups of the following general formula (4):

(4)

(wherein, J represents an atom of XIV group in the periodic table of element; each of $R^2$ and $R^3$ independently represents a hydrogen atom, halogen atom, alkyl group, aralkyl group, aryl group, substituted silyl group, alkoxy group, aralkyloxy group, aryloxy group or di-substituted amino group, and a plurality of $R^2$s may bond mutually to form a ring; m represents an integer of from 0 to 4).

Namely, the transition metal compound of the above-mentioned general formula (1) is preferably transition metal compound of the following general formula (3):

(3)

(wherein, M represents a titanium atom, zirconium atom or hafnium atom in the +3 formal oxide condition; $Cp^1$ represents a group having a cyclopentadiene-type anion skeleton; J represents an atom of XIV group in the periodic table of element; each of $R^2$ and $R^1$ independently represents a hydrogen atom, halogen atom, alkyl group, aralkyl group, aryl group, substituted silyl group, alkoxy group, aralkyloxy group, aryloxy group or di-substituted amino group, and a plurality of $R^2$ s may bond mutually to form a ring; m represents an integer of from 0 to 4; E represents an oxygen atom or sulfur atom; $R^1$ represents an alkyl group, aralkyl group, aryl group or substituted silyl group; each of two Xs independently represents a hydrogen atom, halogen atom, alkyl group, aralkyl group, aryl group, substituted silyl group, alkoxy group, aralkyloxygroup, aryloxy group or di-substituted amino group, and two Xs may bond mutually to form a ring; D represents a neutral ligand coordinated on M; and n represents an integer of from 0 to 2.).

In the above-mentioned general formula (3), J represents an atom of XIV group in the periodic table of element, and as specific examples thereof, a carbon atom, silicon atom, germanium atom and the like are listed, and a carbon atom or a silicon atom is preferable.

In the general formula (3) M, D, n, X and $Cp^1$ are as defined previously in the above-mentioned general formula (1) or (2).

The halogen atom, alkyl group, aralkyl group, aryl group, substituted silyl group, alkoxy group, aralkyloxy group, aryloxy group and di-substituted amino group represented by $R^2$ and $R^3$ in the general formula (3) are as defined for X in the general formula (1). m represents an integer of from 0 to 4 indicating the number of substituent $R^2$ on a benzene ring, preferably an integer of from 0 to 2, and $R^2$ in this case is preferably an alkyl group, alkoxy group or substituted silyl group, more preferably an alkyl group. Each of $R^3$ s independently represents an alkyl group, alkoxy group, aryl group or aryloxy group, or cycloalkanediyl group or silacycloalkanediyl group obtained by combining two $R^3$ and J, further preferably, a methyl group, ethyl group, methoxy group, ethoxy group or phenyl group.

Specific examples of the transition metal compound of the above-mentioned general formula (1) include (methoxycyclopentadienyl)titanium dichloride, (ethoxycyclopentadienyl)titanium dichloride, (n-propoxycyclopentadienyl)titanium dichloride, (isopropoxycyclopentadienyl)titanium dichloride, (n-butoxycyclopentadienyl)titanium dichloride, (t-butoxycyclopentadienyl)titanium dichloride, (trimethylsiloxycyclopentadienyl)titanium dichloride, [(methoxymethyl)cyclopentadienyl]titanium dichloride, [(ethoxymethyl)cyclopentadienyl]titanium dichloride, [(n-propoxymethyl)cyclopentadienyl]titanium dichloride, [(isopropoxymethyl)cyclopentadienyl]titanium dichloride, [(n-butoxymethyl)cyclopentadienyl]titanium dichloride, [(t-butoxymethyl)cyclopentadienyl]titanium dichloride, [(trimethylsiloxymethyl)cyclopentadienyl]titanium dichloride, [(methoxyethyl)cyclopentadienyl]titanium dichloride, [(ethoxyethyl)cyclopentadienyl]titanium dichloride, [(n-propoxyethyl)cyclopentadienyl]titanium dichloride, [(isopropoxyethyl)cyclopentadienyl]titanium dichloride, [(n-butoxyethyl)cyclopentadienyl]titanium dichloride, [(t-butoxyethyl)cyclopentadienyl]titanium dichloride, [(trimethylsiloxyethyl) cyclopentadienyl] titanium dichloride, [(methoxy-n-propyl)cyclopentadienyl] titanium dichloride, [(ethoxy-n-propyl)cyclopentadienyl] titanium dichloride, [(n-propoxy-n-propyl) cyclopentadienyl]titanium dichloride, [(isopropoxy-n-propyl)cyclopentadienyl]titanium dichloride, [(n-butoxy-n-propyl)cyclopentadienyl]titanium dichloride, [(t-butoxy-n-propyl)cyclopentadienyl]titanium dichloride, [(trimethylsiloxy-n-propyl)cyclopentadienyl]titanium dichloride, [(methoxydimethylsilyl)cyclopentadienyl] titanium dichloride, [(ethoxydimethylsilyl) cyclopentadienyl]titanium dichloride, [(n-propoxydimethylsilyl)cyclopentadienyl]titanium dichloride, [(isopropoxydimethylsilyl)cyclopentadienyl]titanium dichloride, [(n-butoxydimethylsilyl)cyclopentadienyl] titanium dichloride, [(t-butoxydimethylsilyl) cyclopentadienyl]titanium dichloride, [(trimethylsiloxydimethylsilyl)cyclopentadienyl]titanium dichloride, [(methoxydimethylsilylmethyl) cyclopentadienyl]titanium dichloride, [(ethoxydimethylsilylmethyl)cyclopentadienyl]titanium dichloride, [(n-propoxydimethylsilylmethyl) cyclopentadienyl]titanium dichloride, [(isopropoxydimethylsilylmethyl)cyclopentadienyl] titanium dichloride, [(n-butoxydimethylsilylmethyl) cyclopentadienyl]titanium dichloride, [(t-butoxydimethylsilylmethyl)cyclopentadienyl]titanium dichloride, [(trimethylsiloxydimethylsilylmethyl) cyclopentadienyl]titanium dichloride, [(methoxydimethylsilylethyl)cyclopentadienyl]titanium dichloride, [(ethoxydimethylsilylethyl)cyclopentadienyl] titanium dichloride, [(n-propoxydimethylsilylethyl) cyclopentadienyl]titanium dichloride, [(isopropoxydimethylsilylethyl)cyclopentadienyl]titanium dichloride, [(n-butoxydimethylsilylethyl)cyclopentadienyl] titanium dichloride, [(t-butoxydimethylsilylethyl) cyclopentadienyl]titanium dichloride, [(trimethylsiloxydimethylsilylethyl)cyclopentadienyl] titanium dichloride, [(methoxydimethylsilyl-n-propyl) cyclopentadienyl]titanium dichloride, [(ethoxydimethylsilyl-n-propyl)cyclopentadienyl]titanium dichloride, [(n-propoxydimethylsilyl-n-propyl) cyclopentadienyl]titanium dichloride, [(isopropoxydimethylsilyl-n-propyl)cyclopentadienyl] titanium dichloride, [(n-butoxydimethylsilyl-n-propyl) cyclopentadienyl]titanium dichloride, [(t-butoxydimethylsilyl-n-propyl)cyclopentadienyl]titanium dichloride, [(trimethylsiloxydimethylsilyl-n-propyl) cyclopentadienyl]titanium dichloride, [(methoxyphenyl) cyclopentadienyl]titanium dichloride, [(ethoxyphenyl) cyclopentadienyl]titanium dichloride, [(n-propoxyphenyl) cyclopentadienyl]titanium dichloride, [(isopropqxyphenyl) cyclopentadienyl]titanium dichloride, [(n-butoxyphenyl) cyclopentadienyl]titanium dichloride, [(t-butoxyphenyl) cyclopentadienyl]titanium dichloride, [(trimethylsiloxyphenyl)cyclopentadienyl]titanium dichloride, [(methoxyphenylmethyl)cyclopentadienyl] titanium dichloride, [(ethoxyphenylmethyl) cyclopentadienyl]titanium dichloride, [(n-propoxyphenylmethyl)cyclopentadienyl]titanium dichloride, [(isopropoxyphenylmethyl)cyclopentadienyl] titanium dichloride, [(n-butoxyphenylmethyl) cyclopentadienyl]titanium dichloride, [(t-butoxyphenylmethyl)cyclopentadienyl]titanium dichloride, [(trimethylsiloxyphenylmethyl)cyclopentadienyl]titanium dichloride, [(methoxyphenylethyl)cyclopentadienyl] titanium dichloride, [(ethoxyphenylethyl)cyclopentadienyl] titanium dichloride, [(n-propoxyphenylethyl) cyclopentadienyl]titanium dichloride, [(isopropoxyphenylethyl)cyclopentadienyl]titanium dichloride, [(n-butoxyphenylethyl)cyclopentadienyl] titanium dichloride, [(t-butoxyphenylethyl) cyclopentadienyl]titanium dichloride, [(trimethylsiloxyphenylethyl)cyclopentadienyl]titanium dichloride, [(methoxyphenyl-n-propyl)cyclopentadienyl] titanium dichloride, [(ethoxyphenyl-n-propyl) cyclopentadienyl]titanium dichloride, [(n-propoxyphenyl-n-propyl)cyclopentadienyl]titanium dichloride, [(isopropoxyphenyl-n-propyl)cyclopentadienyl]titanium dichloride, [(n-butoxyphenyl-n-propyl)cyclopentadienyl] titanium dichloride, [(t-butoxyphenyl-n-propyl) cyclopentadienyl]titanium dichloride, [(trimethylsiloxyphenyl-n-propyl)cyclopentadienyl] titanium dichloride, {[dimethyl(methoxyphenyl)methyl] cyclopentadienyl}titanium dichloride, {[dimethyl (ethoxyphenyl)methyl]cyclopentadienyl}titanium dichloride, {[dimethyl(n-propoxyphenyl)methyl] cyclopentadienyl}titanium dichloride, {[dimethyl (isopropoxyphenyl)methyl]cyclopentadienyl}titanium dichloride, {[dimethyl(n-butoxyphenyl)methyl] cyclopentadienyl}titanium dichloride, {[dimethyl(t-butoxyphenyl)methyl]cyclopentadienyl}titanium dichloride, {[dimethyl(trimethylsiloxyphenyl)methyl] cyclopentadienyl}titanium dichloride, {[dimethyl (methoxyphenyl)silyl]cyclopentadienyl}titanium dichloride, {[dimethyl(ethoxyphenyl)silyl] cyclopentadienyl}titanium dichloride, {[dimethyl(n-propoxyphenyl)silyl]cyclopentadienyl}titanium dichloride, {[dimethyl(isopropoxyphenyl)silyl] cyclopentadienyl}titanium dichloride, {[dimethyl(n-butoxyphenyl)silyl]cyclopentadienyl}titanium dichloride, {[dimethyl(t-butoxyphenyl)silyl]cyclopentadienyl}titanium dichloride, {[dimethyl(trimethylsiloxyphenyl)silyl] cyclopentadienyl)}titanium dichloride, {[(6-methyl-1-methoxyphenyl)methyl]cyclopentadienyl}titanium dichloride, {[(1-ethoxy-6-methylphenyl)methyl] cyclopentadienyl}titanium dichloride, {[(6-methyl-1-n-propoxyphenyl)methyl]cyclopentadienyl}titanium dichloride, {[(6-methyl-1-isopropoxyphenyl)methyl] cyclopentadienyl}titanium dichloride, {[(1-n-butoxy-6-methylphenyl)methyl]cyclopentadienyl}titanium dichloride, {[(1-t-butoxy-6-methylphenyl)methyl]

cyclopentadienyl}titanium dichioride, {[(6-methy-1-trimethylsiloxyphenyl)methyl]cyclopentadieny}titanium dichloride, {[dimethyl(6-methy-1-methoxyphenyl)methyl]cyclopentadieny}titanium dichloride, {[dimethyl(1-ethoxy-6-methylphenyl)methyl]cyclopentadieny}titanium dichloride, {[dimethyl(6-methyl-1-n-propoxyphenyl)methyl]cyclopentadienyl}titanium dichloride, {[dimethyl(6-methyl-1-isopropoxyphenyl)methyl]cyclopentadienyl}titanium dichloride, {[dimethyl(1-n-butoxy-6-methylphenyl)methyl]cyclopentadienyl}titanium dichloride, {[dimethyl(1-t-butoxy-6-methylphenyl)methyl]cyclopentadienyl}titanium dichloride, {[dimethyl(6-methyl-1-trimethylsiloxyphenyl)methyl]cyclopentadienyl}titanium dichloride, {[dimethyl(6-methyl-1-methoxyphenyl)silyl]cyclopentadienyl}titanium dichloride, {[dimethyl(1-ethoxy-6-methylphenyl)silyl]cyclopentadienyl}titanium dichloride, {[dimethyl(6-methyl-1-n-propoxyphenyl)silyl]cyclopentadienyl}titanium dichloride, {[dimethyl(6-methyl-1-isopropoxyphenyl)silyl]cyclopentadienyl}titanium dichloride, {[dimethyl(1-n-butoxy-6-methylphenyl)silyl]cyclopentadienyl}titanium dichloride, {[dimethyl(1-t-butoxy-6-methylphenyl)silyl]cyclopentadienyl}titanium dichloride, {[dimethyl(6-methyl-1-trimethylsiloxyphenyl)silyl]cyclopentadienyl}titanium dichloride, {[(4, 6-dimethyl-1-methoxyphenyl)methyl]cyclopentadienyl)}titanium dichloride, {[(1-ethoxy-4, 6-dimethylphenyl)methyl]cyclopentadienyl}titanium dichloride, {[(4, 6-dimethyl-1-n-propoxyphenyl)methyl]cyclopentadienyl}titanium dichloride, {[(4, 6-dimethyl-1-isopropoxyphenyl)methyl]cyclopentadienyl}titanium dichloride, {[(1-n-butoxy-4, 6-dimethylphenyl)methyl]cyclopentadienyl}titanium dichloride, {[(1-t-butoxy-4, 6-dimethylphenyl)methyl]cyclopentadienyl}titanium dichloride, {[(4, 6-dimethyl-1-trimethylsiloxyphenyl)methyl]cyclopentadienyl}titanium dichloride, {[dimethyl(4, 6-dimethyl-1-methoxyphenyl)methyl]cyclopentadienyl}titanium dichloride, {[dimethyl(1-ethoxy-4 6-dimethylphenyl)methyl]cyclopentadienyl}titanium dichloride, {[dimethyl(4, 6-dimethyl-1-n-propoxyphenyl)methyl]cyclopentadienyl}titanium dichloride, {[dimethyl(4, 6-dimethyl-1-isopropoxyphenyl)methyl]cyclopentadienyl}titanium dichloride, {[dimethyl(1-n-butoxy-4, 6-dimethylphenyl)methyl]cyclopentadienyl}titanium dichloride, {[dimethyl(1-t-butoxy-4, 6-dimethylphenyl)methyl]cyclopentadienyl}titanium dichloride, {[dimethyl(4, 6-dimethyl-1-trimethylsiloxyphenyl)methyl]cyclopentadienyl}titanium dichloride, {[dimethyl(4, 6-dimethyl-1-methoxyphenyl)silyl]cyclopentadienyl}titanium dichloride, {[dimethyl(1-ethoxy-4, 6-dimethylphenyl)silyl]cyclopentadienyl}titanium dichloride, {[dimethyl(4, 6-dimethyl-1-n-propoxyphenyl)silyl]cyclopentadienyl}titanium dichloride, {[dimethyl(4, 6-dimethyl-1-isopropoxyphenyl)silyl]cyclopentadienyl}titanium dichloride, {[dimethyl(1-n-butoxy-4, 6-dimethylphenyl)silyl]cyclopentadienyl}titanium dichloride, {[dimethyl(1-t-butoxy-4, 6-dimethylphenyl)silyl]cyclopentadienyl}titanium dichloride, {[dimethyl(4, 6-dimethyl-1-trimethylsiloxyphenyl)silyl]cyclopentadienyl}titanium dichloride, {[(6-t-butyl-1-methoxyphenyl)methyl]cyclopentadienyl}titanium dichloride, {[(6-t-butyl-1-ethoxyphenyl)methyl]cyclopentadienyl}titanium dichloride, {[(6-t-butyl-1-n-propoxyphenyl)methyl]cyclopentadienyl}titanium dichloride, {[(6-t-butyl-1-isopropoxyphenyl)methyl]cyclopentadienyl}titanium dichloride, {[(6-t-butyl-1-n-butoxyphenyl)methyl]cyclopentadienyl}titanium dichloride, {[(1-t-butoxy-6-t-butylphenyl)methyl]cyclopentadienyl}titanium dichloride, {[(6-t-butyl-1-trimethylsiloxyphenyl)methyl]cyclopentadienyl}titanium dichloride, {[dimethyl(6-t-butyl-1-methoxyphenyl)methyl]cyclopentadienyl}titanium dichloride, {[dimethyl(6-t-butyl-1-ethoxyphenyl)methyl]cyclopentadienyl}titanium dichloride, {[dimethyl(6-t-butyl-1-n-propoxyphenyl)methyl]cyclopentadienyl}titanium dichloride, {[dimethyl(6-t-butyl-1-isopropoxyphenyl)methyl]cyclopentadienyl}titanium dichloride, {[dimethyl(6 t-butyl-1-n-butoxyphenyl)methyl]cyclopentadienyl}titanium dichloride, {[dimethyl(1-t-butoxy-6-t-butylphenyl)methyl]cyclopentadienyl}titanium dichloride, {[dimethyl(6-t-butyl-1-trimethylsiloxyphenyl)methyl]cyclopentadienyl}titanium dichloride, {[dimethyl(6-t-butyl-1-methoxyphenyl)silyl]cyclopentadienyl}titanium dichloride, {[dimethyl(6-t-butyl-1-ethoxyphenyl)silyl]cyclopentadienyl}titanium dichloride, {[dimethyl(6-t-butyl-1-n-propoxyphenyl)silyl]cyclopentadienyl}titanium dichloride, {[dimethyl(6-t-butyl-1-isopropoxyphenyl)silyl]cyclopentadienyl}titanium dichloride, {[dimethyl(6-t-butyl-1-n-butoxyphenyl)silyl]cyclopentadienyl}titanium dichloride, {[dimethyl(1-t-butoxy-6-t-butylphenyl)silyl]cyclopentadienyl}titanium dichloride, {[dimethyl(6-t-butyl-1-trimethylsiloxyphenyl)silyl]cyclopentadienyl}titanium dichloride, {[(4, 6-di-t-butyl-1-methoxyphenyl)methyl]cyclopentadienyl}titanium-dichloride, {[(4, 6-di-t-butyl-1-ethoxyphenyl)methyl]cyclopentadienyl}titanium dichloride, {[(4, 6-di-t-butyl-1-n-propoxyphenyl)methyl]cyclopentadienyl}titanium dichloride, {[(4, 6-di-t-butyl-1-isopropoxyphenyl)methyl]cyclopentadienyl}titanium dichloride, {[(4, 6-di-t-butyl-1-n-butoxyphenyl)methyl]cyclopentadienyl}titanium dichloride, {[(1-t-butoxy-4, 6-di-t-butylphenyl)methyl]cyclopentadienyl}titanium dichloride, {[(4, 6-di-t-butyl-1-trimethylsiloxyphenyl)methyl]cyclopentadienyl}titanium dichloride, {[dimethyl(4, 6-di-t-butyl-1-methoxyphenyl)methyl]cyclopentadienyl}titanium dichloride, {[dimethyl(4, 6-di-t-butyl-1-ethoxyphenyl)methyl]cyclopentadienyl}titanium dichloride, {[dimethyl(4, 6-di-t-butyl-1-n-propoxyphenyl)methyl]cyclopentadienyl}titanium dichloride, { [dimethyl(4, 6-di-t-butyl-1-isopropoxyphenyl)methyl]cyclopentadienyl}titanium dichloride, {[dimethyl(4, 6-di-t-butyl-1-n-butoxyphenyl)methyl]cyclopentadienyl}titanium dichloride, {[dimethyl(1-t-butoxy-4, 6-di-t-butylphenyl)methyl]cyclopentadienyl}titanium dichloride, {[dimethyl(4, 6-di-t-butyl-1-trimethylsiloxyphenyl)methyl]cyclopentadienyl}titanium dichloride, {[dimethyl(4, 6-di-t-butyl-1-methoxyphenyl)silyl]cyclopentadienyl}titanium dichloride, {[dimethyl(4, 6-di-t-butyl-1-ethoxyphenyl)silyl]cyclopentadienyl}titanium dichloride, {[dimethyl(4, 6-di-t-butyl-1-n-propoxyphenyl)silyl]cyclopetadienyl}titanium dichloride, {[dimethyl(4, 6-di-t-butyl-1-isopropoxyphenyl)silyl]cyclopentadienyl}titanium dichloride, {[dimethyl(4, 6-di-t-butyl-1-n-butoxyphenyl)silyl]cyclopentadienyl}titanium dichloride, {[dimethyl(1-t-butoxy-4, 6-di-t-butylphenyl)silyl]cyclopentadienyl}titanium dichloride, {[dimethyl(4, 6-di-t-butyl-1-trimethylsiloxyphenyl)silyl]cyclopentadienyl}titanium dichloride, {[(6-t-butyl-4-methyl-1-methoxyphenyl)methyl]cyclopentadienyl}titanium dichloride, {[(6-t-butyl-1-ethoxy-4-methylphenyl)methyl]cyclopentadienyl}titanium dichloride, {[(6-t-butyl-4-methyl-1-n-propoxyphenyl)methyl]cyclopentadienyl}titanium dichloride, {[(6-t-butyl- 4-methyl-1-isopropoxyphenyl)methyl]cyclopentadienyl}titanium dichloride, {[(1-n-butoxy-6-t-butyl-4-methylphenyl)methyl]cyclopentadienyl}titanium dichloride, {[(1-t-butoxy-6-t-butyl-4-methylphenyl)methyl]cyclopentadienyl}titanium dichloride, {[(6-t-butyl-4-methyl-1-trimethylsiloxyphenyl)methyl]cyclopentadienyl}titanium dichloride, {[dimethyl(6-t-butyl-4-methyl-1-methoxyphenyl)methyl]cyclopentadienyl}titanium dichloride, {[dimethyl(6-t-butyl-1-ethoxy-4-methylphenyl)methyl]cyclopentadienyl}titanium dichloride, {[dimethyl(6-t-butyl-4-methyl-1-n-propoxyphenyl)methyl]cyclopentadienyl}titanium dichloride, {[dimethyl(6-t-butyl-4-methyl-1-isopropoxyphenyl)methyl]cyclopentadienyl}titanium dichloride, {[dimethyl(1-n-butoxy-6-t-butyl-4-methylphenyl)methyl]cyclopentadienyl}titanium dichloride, {[dimethyl(1-t-butoxy-6-t-butyl-4-methylphenyl)methyl]cyclopentadienyl}titanium dichloride, {[dimethyl(6-t-butyl-4-methyl-1-trimethylsiloxyphenyl)methyl]cyclopentadienyl}titanium dichloride, {[dimethyl(6-t-butyl-4-methyl-1-methoxyphenyl)silyl]cyclopentadienyl}titanium dichloride, {[dimethyl(6-t-butyl-1-ethoxy-4-methylphenyl)silyl]cyclopentadienyl}titanium dichloride, {[dimethyl(6-t-butyl-4-methyl-1-n-propoxyphenyl)silyl]cyclopentadienyl}titanium dichloride, {[dimethyl(6-t-butyl-4-methyl-1-isopropoxyphenyl)silyl]cyclopentadienyl}titanium dichloride, {[dimethyl(1-n-butoxy-6-t-butyl-4-methylphenyl)silyl]cyclopentadienyl}titanium dichloride, {[dimethyl(1-t-butoxy-6-t-butyl-4-methylphenyl)silyl]cyclopentadienyl}titanium dichloride, {[dimethyl(6-t-butyl-4-methyl-1-trimethylsiloxyphenyl)silyl]cyclopentadienyl}titanium dichloride, (methylthiocyclopentadienyl)titanium dichloride, (ethylthiocyclopentadienyl)titanium dichloride, (n-propylthiocyclopentadienyl)titanium dichloride, (isopropylthiocyclopentadienyl)titanium dichloride, (n-butylthiocyclopentadienyl)titanium dichloride, (t-butylthiocyclopentadienyl)titanium dichloride, [(methylthiomethyl)cyclopentadienyl]titanium dichloride, [(ethylthiomethyl)cyclopentadienyl]titanium dichloride, [(n-propylthiomethyl)cyclopentadienyl]titanium dichloride, [(isopropylthiomethyl)cyclopentadienyl]titanium dichloride, [(n-butylthiomethyl)cyclopentadienyl]titanium dichloride, [(t-butylthiomethyl)cyclopentadienyl]titanium dichloride, [(methylthioethyl)cyclopentadienyl]titanium dichloride, [(ethylthioethyl)cyclopentadienyl]titanium dichloride, [(n-propylthioethyl)cyclopentadienyl]titanium dichloride, [(isopropylthioethyl)cyclopentadienyl]titanium dichloride, [(n-butylthioethyl)cyclopentadienyl]titanium dichloride, [(t-butylthioethyl)cyclopentadienyl]titanium dichloride, [(methylthio-n-propyl)cyclopentadienyl]titanium dichloride, [(ethylthio-n-propyl)cyclopentadienyl]titanium dichloride, [(n-propylthio-n-propyl)cyclopentadienyl]titanium dichloride, [(isopropylthio-n-propyl)cyclopentadienyl]titanium dichloride, [(n-butylthio-n-propyl)cyclopentadienyl]titanium dichloride, [(t-butylthio-n-propyl)cyclopentadienyl]titanium dichloride, {[dimethyl(methylthiophenyl)methyl]cyclopentadienyl}titanium dichloride, {[dimethyl(ethylthiophenyl)methyl]cyclopentadienyl}titanium dichloride, {[dimethyl(n-propylthiophenyl)methyl]cyclopentadienyl}titanium dichloride, {[dimethyl(isopropylthiophenyl)methyl]cyclopentadienyl}titanium dichloride, {[dimethyl(n-butylthiophenyl)methyl]cyclopentadienyl}titanium dichloride, {[dimethyl(t-butylthiophenyl)methyl]cyclopentadienyl}titanium dichloride, {[dimethyl(trimethylsilylthiophenyl)methyl]cyclopentadienyl}titanium dichloride, {[dimethyl(methylthiophenyl)silyl]cyclopentadienyl}titanium dichloride, {[dimethyl(ethylthiophenyl)silyl]cyclopentadienyl}titanium dichloride, {[dimethyl(n-propylthiophenyl)silyl]cyclopentadienyl}titanium dichloride, {[dimethyl(isopropylthiophenyl)silyl]cyclopentadienyl}titanium dichloride, {[dimethyl(n-butylthiophenyl)silyl]cyclopentadienyl}titanium dichloride, {[dimethyl(t-butylthiophenyl)silyl]cyclopentadienyl}titanium dichloride, {[dimethyl(trimethylsilylthiophenyl)silyl]cyclopentadienyl}titanium dichloride, {[(6-methyl-1-methylthiophenyl)methyl]cyclopentadienyl}titanium dichloride, {[(1-ethylthio-6-methylphenyl)methyl]cyclopentadienyl}titanium dichloride, {[(6-methyl-1-n-propylthiophenyl)methyl]cyclopentadienyl}titanium dichloride, {[(6-methyl-1-isopropylthiophenyl)methyl]cyclopentadienyl}titanium dichloride, {[(1-n-butylthio-6-methylphenyl)methyl]cyclopentadienyl}titanium dichloride, {[(1-t-butylthio-6-methylphenyl)methyl]cyclopentadienyl}titanium dichloride, {[(6-methyl-1-trimethylsilylthiophenyl)methyl]cyclopentadienyl}titanium dichloride, {[dimethyl(6-methyl-1-methylthiophenyl)methyl]cyclopentadienyl}titanium dichloride, {[dimethyl(1-ethylthio-6-methylphenyl)methyl]cyclopentadienyl}titanium dichloride, {[dimethyl(6-methyl-1-n-propylthiophenyl)methyl]cyclopentadienyl}titanium dichloride, {[dimethyl(6-methyl-1-isopropylthiophenyl)methyl]cyclopentadienyl}titanium dichloride, {[dimethyl(1-n-butylthio-6-methylphenyl)methyl]cyclopentadienyl}titanium dichloride, {[dimethyl(1-t-butylthio-6-methylphenyl)methyl]cyclopentadienyl}titanium dichloride, {[dimethyl(6-methyl-1-trimethylsilylthiophenyl)methyl]cyclopentadienyl}titanium dichloride, {[dimethyl(6-methyl-1-methylthiophenyl)silyl]cyclopentadienyl}titanium dichloride, {[dimethyl(1-ethylthio-6-methylphenyl)silyl]cyclopentadienyl}titanium dichloride, {[dimethyl(6-methyl-1-n-propylthiophenyl)silyl]cyclopentadienyl}titanium dichloride, {[dimethyl(6-methyl-1-isopropylthiophenyl)silyl]cyclopentadienyl}titanium dichloride, {[dimethyl(1-n-butylthio-6-methylphenyl)silyl]cyclopentadenyl}titanium dichloride, {[dimethyl(1-t-butylthio-6-methylphenyl)silyl]cyclopentadenyl}titanium dichloride, {[dimethyl(6-methyl-1-trimethylsilylthiophenyl)silyl]cyclopentadienyl}titanium dichloride, {[(4, 6-dimethyl-1-methylthiophenyl)methyl]cyclopentadieny}titanium dichloride, {[(1-ethylthio-4, 6-dimethylphenyl)methyl]cyclopentadienyl}titanium dichloride, {[(4, 6-dimethyl-1-n-propylthiophenyl)methyl]cyclopentadienyl}titanium dichloride, {[(4, 6-dimethyl-1-isopropylthiophenyl)methyl]cyclopentadienyl}titanium dichloride, {[(1-n-butylthio-4, 6-dimethylphenyl)methyl]cyclopentadienyl}titanium dichloride, {[(1-t-butylthio-4, 6-dimethylphenyl)methyl]cyclopentadienyl}titanium dichloride, {[(4, 6-dimethyl-1-trimethylsilylthiophenyl)methyl]cyclopentadienyl}titanium dichloride, {(dimethyl(4, 6-dimethyl-1-methylthiophenyl)methyl]cyclopentadienyl}titanium dichloride, {[dimethyl(1-ethylthio-4, 6-dimethylphenyl)methyl]cyclopentadienyl}titanium dichloride, {[dimethyl(4, 6-dimethyl-1-n-propylthiophenyl)methyl]cyclopentadienyl}titanium dichloride, {[dimethyl(4, 6-dimethyl-1-isopropylthiophenyl)methyl]cyclopentadienyl}titanium dichloride, {[dimethyl(1-n-butylthio-4, 6-dimethylphenyl)methyl]cyclopentadienyl}titanium dichloride, {[dimethyl(1-t- butylthio-4, 6-dimethylphenyl)methyl]cyclopentadienyl}titanium dichloride, {[dimethyl(4,6-dimethyl-1-trimethylsilylthiophenyl)methyl]cyclopentadienyl}titanium dichloride, {[dimethyl(4,6-dimethyl-1-methylthiophenyl)silyl]cyclopentadienyl}titanium dichloride, {[dimethyl(1-ethylthio-4, 6-dimethylphenyl)silyl]cyclopentadienyl}titanium dichloride, {[dimethyl(4,6-dimethyl-1-n-propylthiophenyl)silyl]cyclopentadienyl}titanium dichloride, {[dimethyl(4,6-dimethyl-1-isopropylthiophenyl)silyl]cyclopentadienyl}titanium dichloride, {[dimethyl(1-n-butylthio-4, 6-dimethylphenyl)silyl]cyclopentadienyl}titanium dichloride, {[dimethyl(1-t-butylthio-4, 6-dimethylphenyl)silyl]cyclopentadienyl}titanium dichloride, {[dimethyl(4,6-dimethyl-1-trimethylsilylthiophenyl)silyl]cyclopentadienyl}titanium dichloride, {[(6-t-butyl-1-methylthiophenyl)methyl]cyclopentadienyl}titanium dichloride, {[(6-t-butyl-1-ethylthiophenyl)methyl]cyclopentadienyl}titanium dichloride, {[(6-t-butyl-1-n-propylthiophenyl)methyl]cyclopentadienyl}titanium dichloride, {[(6-t-butyl-1-isopropylthiophenyl)methyl]cyclopentadieny}titanium dichloride, {[(6-t-butyl-1-n-butylthiophenyl)methyl]cyclopentadienyl}titanium dichloride, {[(1-t-butylthio-6-t-butylphenyl)methyl]cyclopentadienyl}titanium dichloride, {[(6-t-butyl-1-trimethylsilylthiophenyl)methyl]cyclopentadienyl}titanium dichloride, {[dimethyl(6-t-butyl-1-methylthiophenyl)methyl]cyclopentadienyl}titanium dichloride, {[dimethyl(6-t-butyl-1-ethylthiophenyl)methyl]cyclopentadienyl}titanium dichloride, {[dimethyl(6-t-butyl-1-n-propylthiophenyl)methyl]cyclopentadienyl}titanium dichloride, {[dimethyl(6-t-butyl-1-isopropylthiophenyl)methyl]cyclopentadienyl}titanium dichloride, {[dimethyl(6-t-butyl-1-n-butylthiophenyl)methyl]cyclopentadienyl}titanium dichloride, {[dimethyl(1-t-butylthio-6-t-butylphenyl)methyl]cyclopentadienyl}titanium dichloride, {[dimethyl(6-t-butyl-1-trimethylsilylthiophenyl)methyl]cyclopentadienyl}titanium dichloride, {[dimethyl(6-t-butyl-1-methylthiophenyl)silyl]cyclopentadienyl}titanium dichloride, {[dimethyl(6-t-butyl-1-ethylthiophenyl)silyl]cyclopentadienyl}titanium dichloride, {[dimethyl(6-t-butyl-1-n-propylthiophenyl)silyl]cyclopentadienyl}titanium dichloride, {[dimethyl(6-t-butyl-1-isopropylthiophenyl)silyl]cyclopentadienyl}titanium dichloride, {[dimethyl(6-t-butyl-1-n-butylthiophenyl)silyl]cyclopentadienyl}titanium dichloride, {[dimethyl(1-t-butylthio-6-t-butylphenyl)silyl]cyclopentadienyl}titanium dichloride, {[dimethyl(6-t-butyl-1-trimethylsilylthiophenyl)silyl]cyclopentadienyl}titanium dichloride, {[(4, 6-di-t-butyl-1-methylthiophenyl)methyl]cyclopentadienyl}titanium dichloride, {[(4, 6-di-t-butyl-1-ethylthiophenyl)methyl]cyclopentadienyl}titanium dichloride, {[(4, 6-di-t-butyl-1-n-propylthiophenyl)methyl]cyclopentadienyl}titanium dichloride, {[(4, 6-di-t-butyl-1-isopropylthiophenyl)methyl]cyclopentadienyl}titanium dichloride, {[(4, 6-di-t-butyl-1-n-butylthiophenyl)methyl]cyclopentadienyl}titanium dichloride, {[(1-t-butylthio-4, 6-di-t-butylphenyl)methyl]cyclopentadienyl}titanium dichloride, {[(4, 6-di-t-butyl-1-trimethylsilylthiophenyl)methyl]cyclopentadienyl}titanium dichloride, {[dimethyl(4,6-di-t-butyl-1-methylthiophenyl)methyl]cyclopentadienyl}titanium dichloride, {[dimethyl(4, 6-di-t-butyl-1-ethylthiophenyl)methyl]cyclopentadienyl}titanium dichloride, {[dimethyl(4, 6-di-t-butyl-1-n-propylthiophenyl)methyl]cyclopentadienyl}titanium dichloride, {[dimethyl(4, 6-di-t-butyl-1-isopropylthiophenyl)methyl]cyclopentadienyl}titanium dichloride, {[dimethyl(4, 6-di-t-butyl-1-n-butylthiophenyl)methyl]cyclopentadienyl}titanium dichloride, {[dimethyl(1-t-butylthio-4, 6-di-t-butylphenyl)methyl]cyclopentadienyl}titanium dichloride, {[dimethyl(4, 6-di-t-butyl-1-trimethylsilylthiophenyl)methyl]cyclopentadienyl}titanium dichloride, {[dimethyl(4, 6-di-t-butyl-1-trimethylthiophenyl)silyl]cyclopentadienyl}titanium dichloride, {[dimethyl(4, 6-di-t-butyl-1-ethylthiophenyl)silyl]cyclopentadienyl}titanium dichloride, {(dimethyl(4, 6-di-t-butyl-1-n-propylthiophenyl)silyl]cyclopentadienyl}titanium dichloride, {[dimethyl(4, 6-di-t-butyl-1-isopropylthiophenyl)silyl]cyclopentadienyl}titanium dichloride, {[dimethyl(4, 6-di-t-butyl-1-n-butylthiophenyl)silyl]cyclopentadienyl}titanium dichloride, {[dimethyl(1-t-butylthio-4, 6-di-t-butylphenyl)silyl]cyclopentadienyl}titanium dichloride, {[dimethyl(4, 6-di-t-butyl-1-trimethylsilylthiophenyl)silyl]cyclopentadienyl}titanium dichloride, {[(6-t-butyl-4-methyl-1-methylthiophenyl)methyl]cyclopentadienyl}titanium dichloride, {[(6-t-butyl-1-ethylthio-4-methylphenyl)methyl]cyclopentadienyl}titanium dichloride, {[(6-t-butyl-4-methyl-1-n-propylthiophenyl)methyl]cyclopentadienyl}titanium dichloride, {[(6-t-butyl-4-methyl-1-isopropylthiophenyl)methyl]cyclopentadienyl}titanium dichloride, {[(1-n-butylthio-6-t-butyl-4-methylphenyl)methyl]cyclopentadienyl}titanium dichloride, {[(1-t-butylthio-6-t-butyl-4-methylphenyl)methyl]cyclopentadienyl}titanium dichloride, {[(6-t-butyl-4-methyl-1-trimethylsilylthiophenyl)methyl]cyclopentadienyl}titanium dichloride, {[dimethyl(6-t-butyl-4-methyl-1-methylthiophenyl)methyl]cyclopentadienyl}titanium dichloride, {[dimethyl(6-t-butyl-1-ethylthio-4-methylphenyl)methyl]cyclopentadienyl}titanium dichloride, {[dimethyl(6-t-butyl-4-methyl-1-n-propylthiophenyl)methyl]cyclopentadienyl}titanium dichloride, {[dimethyl(6-t-butyl-4-methyl-1-isopropylthiophenyl)methy]cyclopentadienyl}titanium dichloride, {[dimethyl(1-n-butylthio-6-t-butyl-4-methylphenyl)methyl]cyclopentadienyl}titanium dichloride, {[dimethyl(1-t-butylthio-6-t-butyl-4-methylphenyl)methyl]cyclopentadienyl}titanium dichloride, {[dimethyl(6-t-butyl-4-methyl-1-trimethylsilylthiophenyl)methyl]cyclopentadienyl}titanium dichloride, {[dimethyl(6-t-butyl-4-methyl-1-methylthiophenyl)silyl]cyclopentadienyl}titanium dichloride, {[dimethyl(6-t-butyl-1-ethylthio-4-methylphenyl)silyl]cyclopentadienyl}titanium dichloride, {[dimethyl(6-t-butyl-4-methyl-1-n-propylthiophenyl)silyl]cyclopentadienyl}titanium dichloride, {[dimethyl(6-t-butyl-4-methyl-1-isopropylthiophenyl)silyl]cyclopentadienyl}titanium dichloride, {[dimethyl(1-n-butylthio-6-t-butyl-4-methylphenyl)silyl]cyclopentadienyl}titanium dichloride, {[dimethyl(1-t-butylthio-6-t-butyl-4-methylphenyl)silyl]cyclopentadienyl}titanium dichloride, {[dimethyl(6-t-butyl-4-methyl-1-trimethylsilylthiophenyl)silyl]cyclopentadienyl}titanium dichloride, [(methoxyphenylthio)cyclopentadienyl]titanium dichloride, [(ethoxyphenylthio)cyclopentadienyl]titanium dichloride, [(n-propoxyphenylthio)cyclopentadienyl]titanium dichloride, [(isopropoxyphenylthio)cyclopentadienyl]titanium dichloride, [(n-butoxyphenylthio)cyclopentadienyl]titanium dichloride, [(t-butoxyphenylthio)

cyclopentadienyl]titanium dichloride, [(trimethylsiloxyphenylthio)cyclopentadienyl]titanium dichloride, [(6-methyl-1-methoxyphenylthio) cyclopentadienyl]titanium dichloride, [(1-ethoxy-6-methylthio)cyclopentadienyl]titanium dichloride, [(6-methyl-1-n-propoxyphenylthio)cyclopentadienyl]titanium dichloride, [(6-methyl-1-isopropoxyphenylthio) cyclopentadienyl]titanium dichloride, [(1-n-butoxy-6-methylphenylthio)cyclopentadienyl]titanium dichloride, [(1-t-butoxy-6-methylphenylthio)cyclopentadienyl]titanium dichloride, [(6-methyl-1-trimethylsiloxyphenylthio) cyclopentadienyl]titanium dichloride, [(4, 6-dimethyl-1-methoxyphenylthio)cyclopentadienyl]titanium dichloride, [(1-ethoxy-4, 6-dimethylphenylthio)cyclopentadienyl] titanium dichloride, [(4, 6-dimethyl-1-n-propoxyphenylthio) cyclopentadienyl]titanium dichloride, [(4, 6-dimethyl-1-isopropoxyphenylthio)cyclopentadienyl]titanium dichloride, [(1-n-butoxy-4, 6-dimethylphenylthio) cyclopentadienyl]titanium dichloride, [(1-t-butoxy-4, 6-dimethylphenylthio)cyclopentadienyl]titanium dichloride, [(4, 6-dimethyl-1-trimethylsiloxyphenylthio) cyclopentadienyl]titanium dichloride, [(6-t-butyl-1-methoxyphenylthio)cyclopentadienyl]titanium dichloride, [(6-t-butyl-1-ethoxyphenylthio)cyclopentadienyl]titanium dichloride, [(6-t-butyl-1-n-propoxyphenylthio) cyclopentadienyl]titanium dichloride, [(6-t-butyl-1-isopropoxyphenylthio)cyclopentadienyl]titanium dichloride, [(6-t-butyl-1-n-butoxyphenylthio) cyclopentadienyl]titanium dichloride, [(1-t-butoxy-6-t-butylphenylthio)cyclopentadienyl]titanium dichloride, [(6-t-butyl-1-trimethylsiloxyphenylthio)cyclopentadienyl] titanium dichloride, [(4, 6-di-t-butyl-1-methoxyphenylthio) cyclopentadienyl]titanium dichloride, [(4, 6-di-t-butyl-1-ethoxyphenylthio)cyclopentadienyl]titaium dichloride, [(4, 6-di-t-butyl-1-n-propoxyphenylthio)cyclopentadienyl] titanium dichloride, [(4, 6-di-t-butyl-1-isopropoxyphenylthio)cyclopentadienyl]titanium dichloride, [(4, 6-di-t-butyl-1-n-butoxyphenylthio) cyclopentadienyl]titanium dichloride, [(1-t-butoxy-4, 6-di-t-butylphenylthio)cyclopentadienyl]titanium dichloride, [(4, 6-di-t-butyl-1-trimethylsiloxyphenylthio)cyclopentadienyl] titanium dichloride, [(6-t-butyl-4-methyl-1-methoxyphenylthio)cyclopentadienyl]titanium dichloride, [(6-t-butyl-1-ethoxy-4-methylphenylthio)cyclopentadienyl] titanium dichloride, [(6-t-butyl-4-methyl-1-n-propoxyphenylthio)cyclopentadienyl]titanium dichloride, [(6-t-butyl-4-methyl-1-isopropoxyphenylthio) cyclopentadienyl]titanium dichloride, [(1-n-butoxy-6-t-butyl-4-methylphenylthio)cyclopentadienyl]titanium dichloride, [(1-t-butoxy-6-t-butyl-4-methylphenylthio) cyclopentadienyl]titanium dichloride, [(6-t-butyl-4-methyl-1-trimethylsiloxyphenylthio)cyclopentadienyl]titanium dichloride, [(methoxyphenoxy)cyclopentadienyl]titanium dichloride, [(ethoxyphenoxy)cyclopentadienyl]titanium dichloride, [(n-propoxyphenoxy)cyclopentadienyl]titanium dichloride, [(isopropoxyphenoxy)cyclopentadienyl]titanium dichloride, [(n-butoxyphenoxy)cyclopentadienyl]titanium dichloride, [(t-butoxyphenoxy)cyclopentadienyl]titanium dichloride, [(trimethylsiloxyphenoxy)cyclopentadienyl] titanium dichloride, [(6-methyl-1-methoxyphenoxy) cyclopentadienyl]titanium dichloride, [(1-ethoxy-6-methylphenoxy)cyclopentadienyl]titanium dichloride, [(6-methyl-1-n-propoxyphenoxy)cyclopentadienyl]titanium dichloride, [(6-methyl-1-isopropoxyphenoxy) cyclopentadienyl]titanium dichloride, [(1-n-butoxy-6-methylphenoxy)cyclopentadienyl]titanium dichloride, [(1-t-butoxy-6-methylphenoxy)cyclopentadienyl]titanium dichloride, [(6-methyl-1-trimethylsiloxyphenoxy) cyclopentadienyl]titanium dichloride, [(4, 6-dimethyl-1-methoxyphenoxy)cyclopentadienyl]titanium dichloride, [(1-ethoxy-4, 6-dimethylphenoxy)cyclopentadienyl]titanium dichloride, [(4, 6-dimethy-1-n-propoxylphenoxy) cyclopentadienyl]titanium dichloride, [(4, 6-dimethy-1-isopropoxylphenoxy)cyclopentadienyl]titanium dichloride, [(1-n-butoxy-4, 6-dimethylphenoxy)cyclopentadienyl] titanium dichloride, [(1-t-butoxy-4, 6-dimethylphenoxy) cyclopentadienyl]titanium dichloride, [(4, 6-dimethyl-1-trimethylsiloxyphenoxy)cyclopentadienyl]titanium dichloride, [(6-t-butyl-1-methoxyphenoxy) cyclopentadienyl]titanium dichloride, [(6-t-butyl-1-ethoxyphenoxy)cyclopentadienyl]titanium dichloride, [(6-t-butyl-1-n-propoxyphenoxy)cyclopentadienyl]titanium dichloride, [(6-t-butyl-1-isopropoxyphenoxy) cyclopentadienyl]titanium dichloride, [(6-t-butyl-1-n-butoxyphenoxy)cyclopentadienyl]titanium dichloride, [(1-t-butoxy-6-t-butylphenoxy)cyclopentadienyl]titanium dichloride, [(6-buyl-1-trimethylsiloxyphenoxy) cyclopentadienyl]titanium dichloride, [(4, 6-di-t-butyl-1-methoxyphenoxy)cyclopentadienyl]titanium dichloride, [(4, 6-di-t-butyl-1-ethoxyphenoxy)cyclopentadienyl]titanium dichloride, [(4, 6-di-t-butyl-1-n-propoxyphenoxy) cyclopentadienyl]titanium dichloride, [(4, 6-di-t-butyl-1-isopropoxyphenoxy)cyclopentadienyl]titanium dichloride, [(4, 6-di-t-butyl-1-n-butoxyphenoxy)cyclopentadienyl] titanium dichloride, [(1-t-butoxy-4, 6-di-t-butylphenoxy) cyclopentadienyl]titanium dichloride, [(4, 6-di-t-butyl-1-trimethylsiloxyphenoxy)cyclopentadienyl]titanium dichloride, [(6-t-butyl-4-methyl-1-methoxyphenoxy) cyclopentadienyl]titanium dichloride, [(6-t-butyl-1-ethoxy-4-methylphenoxy)cyclopentadienyl]titanium dichloride, [(6-t-butyl-4-methyl-1-n-propoxyphenoxy) cyclopentadienyl]titanium dichloride, [(6-t-butyl-4-methyl-1-isopropoxyphenoxy)cyclopentadienyl]titanium dichloride, [(1-n-butoxy-6-t-butyl-4-methylphenoxy) cyclopentadienyl]titanium dichloride, [(1-t-butoxy-6-t-butyl-4-methylphenoxy)cyclopentadienyl]titanium dichloride, [(6-t-butyl-4-methyl-1-trimethylsiloxyphenoxy) cyclopentadienyl]titanium dichloride and the like, transition metal compounds obtained by substituting titanium in these compounds with zirconium or hafnium, transition metal compounds obtained by substituting chloride in these compounds with bromide, iodide, dimethylamide, diethylamide, n-butoxide or isopropoxide, transition metal compounds obtained by substituting cyclopentadienyl in these compounds with dimethylcyclopentadienyl, trimethylcyclopentadienyl, tetramethylcyclopentadienyl, n-butylcyclopentadienyl, tert-butyldimethylsilylcyclopentadienyl, indenyl, tetrahydroindenyl, fluorenyl or octahydrofluorenyl.

The transition metal compound(A) of the present invention can be produced by methods described below.

Ligands required in synthesis of the transition metal compound can be synthesized by methods disclosed in, for example, EP-A-0842939, Q. Huang, et al., Transition Metal. Chem. 1990, 15, 483, and the like.

And, the transition metal compound (A) can be obtained by reacting a metal salt obtained by reacting a ligand obtained by the above-described method with an alkaline metal compound or alkaline earth metal compound, with a compound of a trivalent transition metal of the $4^{th}$ group of the Periodic Table of the Elements, or a mixture of a compound of a tetravalent transition metal of the $4^{th}$ group and a reducing agent.

The catalyst for addition polymerization of the present invention is a catalyst for addition polymerization obtained by allowing the transition metal compound (A) to contact with a co-catalyst for activation. The catalyst for addition polymerization of the present invention is preferably a catalyst for addition polymerization obtained by allowing the transition metal compound (A) to contact with the following (B) and/or the following (C):

(B): one or more aluminum compounds selected from the following (B1) to (B3):
(B1) organic aluminum compounds of the general formula $E^1_a AlZ_{3-a}$,
(B2) cyclic aluminoxanes having a structure of the general formula $\{-Al(E^2)-O-\}_b$,
(B3) linear aluminoxanes having a structure of the general formula $E^3 \{-Al(E^3)-O-\}_c AlE^3_2$, wherein, each of $E^1$, $E^2$ and $E^3$ represents a hydrocarbon group, and all $E^1$ s, all $E^2$ s or all $E^3$ s may be the same or different; Z represents a hydrogen atom or halogen atom and all Zs may be the same or different; a represents a number satisfying $0 < a \leq 3$, b represents an integer of 2 or more; and c represents an integer of 1 or more, (C) one or more boron compounds selected from the following (C1) to (C3):
(C1) boron compounds of the general formula $BQ^1 Q^2 Q^3$,
(C2) boron compounds of the general formula $G^+(BQ^1 Q^2 Q^3 Q^4)^-$,
(C3) boron compounds of the general formula $(L-H)^+ (BQ^1 Q^2 Q^3 Q^4)^-$, wherein B represents a trivalent boron atom; $Q^1$ to $Q^4$ represent a halogen atom, hydrocarbon group, halogenated hydrocarbon group, substituted silyl group, alkoxy group or di-substituted amino group and they may be the same or different; $G^+$ represents an inorganic or organic cation; L represents a neutral Lewis base; and $(L-H)^+$ represents a Brønsted acid.

Such a catalyst for addition polymerization will be further illustrated in detail below.

(B) Aluminum Compounds

As the hydrocarbon group represented by $E^1$, $E^2$ and $E^3$ in the aluminum compounds (B1), (B2) and (B3) mentioned above, respectively, a hydrocarbon group having 1 to 8 carbon atoms is preferable, and an alkyl group is more preferable.

Specific examples of the organic aluminum compound (B1) of the general formula $E^1_a AlZ_{3-a}$ include trialkylaluminums such as trimethylaluminum, triethylaluminum, tripropylaluminum, triisobutylaluminum, trihexylaluminum and the like; dialkylaluminum chlorides such as dimethylaluminum chloride, diethylaluminum chloride, dipropolyaluminum chloride, diisobutylaluminum chloride, dihexylaluminum chloride and the like; alkylaluminum dichlorides such as methylaluminum dichloride, ethylaluminum dichloride, propylaluminum dichloride, isobutylaluminum dichloride, hexylaluminum dichloride and the like; dialkylaluminum hydrides such as dimethylaluminum hydride, diethylaluminum hydride, dipropylaluminum hydride, diisobutylaluminum hydride, dihexylaluminum hydride and the like, etc.

Trialkylaluminums are preferable, and triethylaluminum or triisobutylaluminum is more preferable.

As specific examples of $E^2$ and $E^3$ in cyclic aluminoxanes (B2) having a structure of the general formula $\{-Al(E^2)-O-\}_b$, and linear aluminoxanes (B3) having a structure of the general formula $E^3 \{-Al(E^3)-O-\}_c AlE^3_2$, respectively, alkyl groups such as a methyl group, ethyl group, n-propyl group, isopropyl group, n-butyl group, isobutyl group, n-pentyl group, neopentyl group and the like can be exemplified. b in an integer of 2 or more, and c is an integer of 1 or more. Preferably, $E^2$ and $E^3$ are a methyl group or isobutyl group, b is 2 to 40, and c is 1 to 40.

The above-mentioned aluminoxane is produced by various methods. The method is not particularly restricted, and it may be advantageously carried out according to a known method. For example, a trialkylaluminum (for example, trimethylaluminum) is dissolved in a suitable organic solvent (benzene, aliphatic hydrocarbon or the like) to prepare a solution which is allowed to contact with water. Alternatively, there is exemplified a method in which a trialkylaluminum (for example, trimethylaluminum) is allowed to contact with a metal salt containing crystal water (for example, copper sulfate hydrate or the like).

The aluminoxane produced by such methods is usually supposed to be a mixtures of a cyclic aluminoxane and a linear aluminoxane.

(C) Boron Compound

As the boron compound (C), one or more boron compounds selected from (C1) boron compounds of the general formula $BQ^1 Q^2 Q^3$, (C2) boron compounds of the general formula $G^+(BQ^1 Q^2 Q^3 Q^4)^-$, and (C3) boron compounds of the general formula $(L-H)^+(BQ^1 Q^2 Q^3 Q^4)^1$ are used, in the present invention.

In the boron compound (C1) of the general formula $BQ^1 Q^2 Q^3$, B represents a trivalent boron atom, and $Q^1$ to $Q^3$ represent a halogen atom, hydrocarbon group, halogenated hydrocarbon group, substituted silyl group, alkoxy group or di-substituted amino group, and they may be the same or different. $Q^1$ to $Q^3$ preferably represent a halogen atom, a hydrocarbon group having 1 to 20 carbon atoms, a halogenated hydrocarbon group having 1 to 20 carbon atoms, a substituted silyl group having 2 to 20 carbon atoms, an alkoxy group having 1 to 20 carbon atoms, or an amino group having 1 to 20 carbon atoms, and $Q^1$ to $Q^3$ more preferably represent a halogen atom, a hydrocarbon group having 1 to 20 carbon atoms or a halogenated hydrocarbon group having 1 to 20 carbon atoms. Further preferably, $Q^1$ to $Q^4$ represent a fluorinated hydrocarbon group having 1 to 20 carbon atoms containing at least one fluorine atom, and particularly preferably, $Q^1$ to $Q^4$ represent a fluorinated aryl group having 6 to 20 carbon atoms containing at least one fluorine atom.

Specific examples of the compound (C1) include tris(pentafluorophenyl)borane, tris(2,3,5,6-tetrafluorophenyl)borane, tris(2,3,4,5-tetrafluorophenyl)borane, tris(3,4,5-trifluorophenyl)borane, tris(2,3,4-trifluorophenyl)borane, phenylbis(pentafluorophenyl)borane and the like, and tris(pentafluorophenyl)borane is most preferable.

In the boron compound (C2) of the general formula $G^+(BQ^1 Q^2 Q^3 Q^4)^-$, $G^+$ represents an inorganic or organic cation, B represents a trivalent boron atom, and $Q^1$ to $Q^4$ are as defined for $Q^1$ to $Q^3$ in the above-mentioned (C1).

As specific examples of an inorganic cation $G^+$ in the compound of the general formula $G^+(BQ^1 Q^2 Q^3 Q^4)^-$, a ferrocenium cation, alkyl-substituted ferrocenium cation, silver cation and the like are listed, and as specific examples of an organic cation $G^+$ in the compound, a triphenylmethyl cation and the like are listed. $G^+$ represents preferably a carbenium cation, and particularly preferably a triphenylmethyl cation. As $(BQ^1 Q^2 Q^3)^-$, there are listed tetrakis(pentafluorophenyl)borate, tetrakis(2,3,5,6-tetrafluoropheny)borate, tetrakis(2,3,4,5-tetrafluorophenyl)borate, tetrakis(3,4,5-trifluorophenyl)borate, tetrakis(2,3,4-trifluorophenyl)borate, phenyltris(pentafluorophenyl)borate, tetrakis(3,5-bistrifluoromethylphenyl)borate and the like.

As specific combinations thereof, ferrocenium tetrakis(pentafluorophenyl)borate, 1,1'-dimethylferrocenium tetrakis(pentafluorophenyl)borate, silver tetrakis(pentafluorophenyl)borate, tripheylmethyltetrakis(pentafluorophenyl)borate, triphenylmethyltetrakis(3,5-bistrifluoromethylphenyl)bora te, and the like are listed, and triphenylmethyltetrakis(pentafluorophenyl)borate is most preferable.

In the boron compound (C3) of the general formula $(L—H)^+(BQ^1 Q^2 Q^3 Q^4)^-$, L representsaneutralLewis base and $(L—H)^+$ represents a Brønsted acid, B represents a trivalent boron atom, and $Q^1$ to $Q^4$ are as defined for $Q^1$ to $Q^3$ in the above-mentioned Lewis acid (C1).

As specific examples of the Brønsted acid $(L—H)^+$ in the compound of the general formula $(L—H)^+(BQ^1 Q^2 Q^3 Q^4)^-$, trialkyl-substituted ammoniums, N,N-dialkylaniliniums, dialkylammoniums, triarylphosphoniums and the like are listed, and as $(BQ^1 Q^2 Q^3 Q^4)^-$, the same moieties as described above are listed.

As specific combinations thereof, triethylammoniumtetrakis(pentafluorophenyl)borate, tripropylammonium tetrakis(pentafluorophenyl)borate, tri(n-butyl)ammoniumtetrakis(pentafluorophenyl)borate, tri(n-butyl)ammonium tetrakis(3,5-bistrifluoromethylphenyl)borate, N,N-dimethylaniliniumtetrakis(pentafluorophenyl)borate, N,N-diethylanilinium tetrakis(pentafluorophenyl)borate, N,N-2,4,6-pentamethylaniliniumtetrakis(pentafluorophenyl) borate, N,N-dimethylaniliniumtetrakis(3,5-bistrifluoromethylphenyl)borate, diisopropylammoniumtetrakis(pentafluorophenyl)borate, dicyclohexyammoniumtetrakis(pentafluorophenyl)borate, riphenylphosphoniumtetrakis(pentafluorophenyl)borate, tri(methylphenyl)phosphoniumtetrakis(pentafluorophenyl)borate, tri(dimethylphenyl)phosphoniumtetrakis(pentafluorophenyl) borate and the like are listed, and most preferable is tri(n-butyl)ammonium tetrakis(pentafluorophenyl)borate, or N,N-dimethylaniliniumtetrakis(pentafluorophenyl)borate.

Contact in preparation of a catalyst for addition polymerization by bringing the transition metal compound (A) into contact with a co-catalyst for activation in the present invention may be conducted by any means providing the transition metal compound (A) and the co-catalyst for activation are contacted to form a catalyst, and there are adopted a method in which a transition metal compound and a co-catalyst for activation are previously diluted with a solvent or not diluted, before they are mixed for mutual contact, and a method in which a transition metal compound and a co-catalyst for activation are separately fed into a polymerization vessel for mutual contact thereof. As the co-catalyst for activation, a plurality of compounds may be combined and used, however, it is needless to say that a part of which may be previously mixed and used, or they may be separately fed into a polymerization vessel and used.

It is desirable to use components so that the molar ratio of the aluminum compound (B)/transition metal compound (A) is from 0.1 to 10000, preferably from 5 to 2000, and the molar ratio of the boron compound (C)/transition metal compound (A) is from 0.01 to 100, preferably from 0.5 to 10.

The concentrations of components when they are used in the form of a solution, or suspension or slurry in a solvent are appropriately selected depending on the ability of an apparatus for feeding components into a polymerization reactor, and it is generally desirable that the concentration of the transition metal compound (A) is usually from 0.001 to 200 mmol/L, more preferably from 0.001 to 100 mmol/L, further preferably from 0.05 to 50 mmol/L, the concentration of the aluminum compound (B) is, in terms of an Al atom, usually from 0.01 to 5000 mmol/L, more preferably from 0.1 to 2500 mmol/L, further preferably 0.1 to 2000 mmol/L, and the concentration of the boron compound (C) is usually from 0.001 to 500 mmol/L, more preferably from 0.01 to 250 mmol/L, further preferably from 0.05 to 100 mmol/L. [Polymerization]

In the present invention, a catalyst for addition polymerization obtained by bringing the above-mentioned transition metal compound (A) into contact with the aluminum compound (B) and/or the boron compound (C) is used. When a catalyst for addition polymerization obtained by bringing the transition metal compound (A) into contact with the aluminum compound (B) is used, the above-mentioned aluminoxane (B2) and/or linear aluminoxane (B3) is preferably used as (B). As other preferable embodiment of the catalyst for addition polymerization, catalysts for addition polymerization obtained by contact of the transition metal compound (A) and, the aluminum compound (B) and the boron compound (C) are listed, and the above-mentioned (B1) is easily used as (B) in this case.

As monomer applicable in polymerization, addition polymerizable compounds such as olefins having 2 to 20 carbon atoms, particularly, ethylene, α-olefins having 3 to 20 carbon atoms, diolefins having 4 to 20 carbon atoms, and the like can be used, and two or more monomers can be used simultaneously. Specific examples of the olefin include linear olefins such as ethylene, propylene, butene-1, pentene-1, hexene-1, heptene-1, octene-1, nonene-1, decene-land the like, branched olefins such as 3-methylbutene-1,3-methylpentene-1, 4-methylpentene-1,5-methyl-hexene-1 and the like, and diolefins such as 1,3-butadiene and isoprene, and vinylcyclohexane are also listed, however, the present invention should not be limited by these compounds. As specific examples of combinations of monomers in conducting copolymerization, ethylene and propylene, ethylene and butene-1, ethylene and hexene-1, ethylene and octane-1, ethylene and 5-hexene-1-ol, propylene and butene-1, ethylene-vinylcyclohexane, and the like are exemplified, however, the present invention should not be limited by these combinations.

The polymerization method should also not be limited particularly, and for example, solvent polymerization using as a solvent an aliphatic hydrocarbon such as butane, pentane, hexane, heptane, octane and the like, an aromatic hydrocarbon such as benzene, toluene and the like, or a halogenated hydrocarbon such as methylene dichloride and the like, or slurry polymerization, gas phase polymerization in gaseous monomers, and the like can be used, and any of continuous polymerization and batch-wise polymerization is possible.

The polymerization temperature can be usually from −50° C. to 200° C., and particularly, preferably from −20° C. to 100° C., and the polymerization pressure is usually preferably from normal pressure to 60, kg/cm² G. The polymerization time is generally determined appropriately depending on the kind of the intended polymer, and the reaction apparatus, and usually, it can be from 1 minute to 20 hours. Further, in the present invention, a chain transfer agent such as hydrogen or the like can also be added for controlling the molecular weight of a polymer.

The following examples and comparative examples will illustrate the present invention further in detail below, but do not limit the scope of the present invention.

The properties of polymers in examples were measured by the following methods.
(1) Intrinsic viscosity [η]: It was measured by using a Ubbellohde viscometer in a tetralin solution at 130° C.
(2) Content of repeating units derived from α-olefin in a copolymer:

It was measured from the specific absorptions of ethylene and α-olefin using an infrared spectrophotometer (IR-810, manufactured by Nippon Bunko Kogyo K.K.), and represented in terms of short chain branch (SCB) numbers per 1000 carbons. In addition, in a content of a comonomer other than α-olefin, the content was measured in the same manner.
(3) Melting point of copolymer: It was measured by using Seiko SSC-5200 under the following conditions.

Heating: 40° C. to 150° C. (10° C./min.), kept for 5 minutes

Cooling:150° C. to 10° C. (5° C./min.), kept for 10 minutes

Measurement: 10° C. to 160° C. (5° C./min.)
(4) Molecular weight and molecular weight distribution: These were measured by using gel permeation chromatography (manufactured by Waters, 150, C) under the following conditions.

Column: TSK gel GMH—HT

Measurement temperature: set at 145° C.

Measurement concentration: 10 mg/10 ml-orthodichlorobenzene

The molecular weight distribution was evaluated by the ratio (Mw/Mn) of the weight average molecular weight (Mw) to the number average molecular weight (Mn).

EXAMPLE 1

(1) Synthesis of 1-Bromo-3-tert-butyl-5-Methyl-2-Phenol

In a 500 ml four-necked flask equipped with a stirrer, 20.1 g (123 mmol) of 2-tert-butyl-4-methylphenol was dissolved in 150 ml of toluene, subsequently, 25.9 ml (18.0 g, 246 mmol) of tert-butylamine was added to the solution, under nitrogen atmosphere. This solution was cooled to −70° C., to this was added 10.5 ml (32.6 g, 204 mmol) of bromine. This solution was stirred for 2 hours while maintaining at −70° C. Subsequently, the solution was heated to room temperature, and washed with 100 ml of 10 % hydrochloric acid three times. After washing, the resulted organic layer was dried by anhydrous sodium sulfate, the solvent was removed by using an evaporator, then, the layer was purified using a silica gel column, to obtain 18.4 g (75.7 mmol) of colorless oil: 1-bromo-3-tert-butyl-5-methyl-2-phenol. The yield was 62 %.

(2) Synthesis of 1-Bromo-3-tert-butyl-2-methoxy-5-methylbenzene

In a 100 ml four-necked flask equipped with a stirrer, 13.9 g (57.2 mmol) of 1-bromo-3-tert-butyl-5-methyl-2-phenol synthesized in (1) above was dissolved in 40 ml of acetonitrile, subsequently, 3.8 g (67.9 mmol) of potassium hydroxide was added to the solution, under nitrogen atmosphere. Further, 17.8 ml (40.6 g, 286 mmol) of methyl iodide was added, and the mixture was stirred continuously for 12 hours. Then, the solvent was removed by using an evaporator, 40 ml of hexane was added to the residue, and hexane soluble portions were extracted. The extraction was repeated three times. The solvent was removed from the extracted fraction, to obtain 13.8 g (53.7 mmol) of pale yellow oil: 1-bromo-3-tert-butyl-2-methoxy-5-methylbenzene. The yield was 94 %.

(3) Synthesis of Chlorodimethyl(3-tert-butyl-2-methoxy-5-methylphenyl)silane

Into a solution composed of 31.5 ml of tetrahydrofuran, 139 ml of hexane and 45 g of 1-bromo-3-tert-butyl-2-methoxy-5-methylbenzene synthesized in the same method as in the above-mentioned process (2) was added 115 ml of a 1.6 mol/liter solution of n-butyllithium in hexane dropwise at −40° C. over 20 minutes. The resulted mixture was kept at −40° C. for 1 hour, then, 31.5 ml of tetrahydrofuran was added dropwise.

Into a solution composed of 131 g of dichlorodimethyl-silane and 306 ml of hexane was added the mixture obtained above dropwise at −40° C. The resulted mixture was heated up to room temperature over 2 hours, further, stirred for 12 hours at room temperature.

From the reaction mixture, the solvent and excess dichlorodimethylsilane were distilled off under reduced pressure, and hexane-soluble portions were extracted from the residue using hexane, and the solvent was distilled off from the resulted hexane solution, to obtain 41.9 g of chlorodimethyl (3-tert-butyl-2-methoxy-5-methylphenyl) silane in the form of pale yellow oil. The yield was 84 %.

(4) Synthesis of (tetramethylcyclopentadienyl) dimethyl (3-tert-butyl-2-methoxy-5-methylphenyl) silane Into a solution composed of 5.24 g of chlorodimethyl(3-tert-butyl-2-methoxy-5-methylphenyl)silane synthesized in (3) above and 50 ml of tetrahydrofuran was added 2.73 g of tetramethylcyclopentadienyllithium dropwise at −35° C., and the mixture was heated up to room temperature over 2 hours, and further stirred for 10 hours at room temperature.

The solvent was distilled off under reduced pressure from the resulted reaction mixture, and hexane-soluble portions were extracted from the residue using hexane, and the solvent was distilled off under reduced pressure from the resulted hexane solution, to obtain 6.69 g of (tetramethylcyclopentadienyl)dimethyl(3-tert-butyl-2-methoxy-5-methylphenyl)silane in the form of yellow oil. The yield was 97 %.

(5) Synthesis of [dimethyl(3-tert-butyl-2-methoxy-5-methylphenyl)silyl (tetramethylcyclopentadienyl)] titanium Dichloride Into a solution composed of 2.00 g of (tetramethylcyclopentadienyl)dimethyl(3-tert-butyl-2-methoxy-5-methylphenyl)silane synthesized in (4) above, 20 g of toluene and 1.25 g of triethylamine was added 3.84 ml of a 1.61 mol/liter solution of n-butyllithium in hexane dropwise at 0, then, the solution was heated up to room temperature over 2 hours, further maintained at room temperature for 12 hours.

20.9 g of suspension of 2.09 g of titanium trichloride tripyridine in toluene was added dropwise at 0° C. Under nitrogen atmosphere into the mixture obtained above, then, the mixture was heated up to room temperature over 1 hour, then, the mixture was heated under reflux for 10 hours.

The reaction mixture was filtrated, the solvent was distilled off from the filtrate, and the residue was re-crystallized from a toluene-hexane mixed solvent, to obtain 0.46 g of [dimethyl(3-tert-butyl-2-methoxy-5-methylphenyl)silyl(tetramethylcyclopentadienyl)]titanium dichloride in the form of a pale green fine crystal. The yield was 17 %.

The spectral data is as shown below.
Mass spectrum (CI, m/e) 473

An autoclave having an inner volume of 1 liter equipped with a stirrer as a reactor was dried under vacuum and purged with argon, then, 300 ml of toluene as a solvent was charged therein, and the reactor was heated up to 60° C. After the heating, ethylene was fed while controlling the ethylene pressure at 6 kg/cm², and after the system was stabilized, 1.0 mmol of triisobutylaluminum was added, subsequently, 2.0 μmol of [dimethyl(3-tert-butyl-2-methoxy-5-methylphenyl)silyl(tetramethylcyclopentadienyl)]titanium dichloride synthesized in (5) above was added, then, 6.0 μmol of triphenylcarbeniumtetrakis(pentafluorophenyl)borate was added. Polymerization was carried out for 60 minutes while controlling the temperature at 60° C. The temperature in the reactor increased by 3.1° C. by the initial heat generation in this polymerization.

As a result of polymerization, an ethylene homopolymer having a melting point of 133.1° C. was produced at a rate of 8.7×10⁶ g per one hour per 1 mol of the titanium compound.

EXAMPLE 2

An autoclave having an inner volume of 0.4 liter equipped with a stirrer as a reactor was dried under vacuum and purged with argon, then, 190 ml of toluene as a solvent and 10 ml of hexene-1 as an α-olefin were charged into this, and the reactor was heated up to 60° C. After temperature raise, ethylene was fed while controlling the ethylene pressure at 6 kg/cm², and after the system was stabilized, 0.5 mmol of triisobutylaluminum was added, subsequently, 1.0 μmol of [dimethyl(3-tert-butyl-2-methoxy-5-methylphenyl)silyl(tetramethylcyclopentadienyl)]titanium dichloride was added, then, 3.0 μmol of triphenylcarbeniumtetrakis(pentafluorophenyl)borate was added. Polymerization was carried out for 60 minutes while controlling the temperature at 60° C. The temperature in the reactor increased by 1.9° C. by the initial heat generation in this polymerization.

As a result of polymerization, an ethylene-hexene-1 copolymer having an SCB of 20.6, a [η] of 1.17 dl/g, a molecular weight (Mw) of 7.6×10⁴, a molecular weight distribution (Mw/Mn) of 2.2 and a melting point of 110.3° C. was produced at a rate of 1.5×10⁷ g per one hour per 1 mol of the titanium compound.

COMPARATIVE EXAMPLE 1

An autoclave having an inner volume of 0.4 liter equipped with a stirrer as a reactor was dried under vacuum and purged with argon, then, 190 ml of toluene as a solvent and 10 ml of hexene-1 as an α-olefin were charged into this, and the reactor was heated up to 60° C. After the heating, ethylene was fed while controlling the ethylene pressure at 6 kg/cm², and after the system was stabilized, 0.50 mmol of triisobutylaluminum was added, subsequently, 1.0 μmol of [dimethyl(3-tert-butyl-2-methoxy-5-methylphenyl)silyl(tetramethylcyclopentadienyl)]titanium dichloride was added, then, 3.0 μmol of triphenylcarbeniumtetrakis(pentafluorophenyl)borate was added. Polymerization was carried out for 60 minutes while controlling the temperature at 60° C. The temperature in the reactor increased by 11.5° C. by the initial heat generation in this polymerization.

As a result of polymerization; an ethylene-hexene-1 copolymer was produced at a rate of 1.1×10⁷ g per one hour per 1 mol of the titanium compound.

EXAMPLE 3

An autoclave having an inner volume of 0.4 liter equipped with a stirrer as a reactor was dried under vacuum and purged with argon, then, 190 ml of toluene as a solvent and 10 ml of hexene-1 as an α-olefin were charged into this, and the reactor was heated up to 60° C. After temperature raise, ethylene was fed while controlling the ethylene pressure at 6 kg/cm², and after the system was stabilized, an MMAO type 3 A toluene solution manufactured by Tosoh-Akzo Company, Ltd., was charged in an amount of 1.0 mmol in terms of Al, subsequently, 1.0 μmol of [dimethyl(3-tert-butyl-2-methoxy-5-methylphenyl)silyl(tetramethylcyclopentadienyl)]titanium dichloride was added. Polymerization was carried out for 60 minutes while controlling the temperature at 60° C. The temperature raise in the reactor by the initial heat generation in this polymerization was not observed.

As a result of polymerization, an ethylene-hexene-1 copolymer having an SCB of 14.8, a [η] of 1.71 dl/g, a molecular weight (Mw) of 7.1×10⁴, a molecular weight distribution (Mw/Mn) of 1.9 and a melting point of 114.7° C. was produced at a rate of 3.0×10⁶ g per one hour per 1 mol of the titanium compound.

EXAMPLE 4

Polymerization was carried out in the same manner as in Example 2 except that hexane-1 used was changed to 10 g of butene-1. The temperature in the reactor increased by 2.6° C. by the initial heat generation in this polymerization.

As a result of polymerization, an ethylene-butene-1 copolymer having an SCB of 15.2, a [η] of 1.26 dl/g, a molecular weight (Mw) of 7.5×10⁴, a molecular weight distribution (Mw/Mn) of 2.7 and a melting point of 93.9° C. was produced at a rate of 1.5×10⁷ g per one hour per 1 mol of the titanium compound.

EXAMPLE 5

Polymerization was carried out in the same manner as in Example 2 except that triisobutylaluminum was changed to triethylaluminum of the same molar amount. The temperature in the reactor increased by 0.3° C. by the initial heat generation in this polymerization.

As a result of polymerization, an ethylene-hexene-1 copolymer having an SCB of 12.7, a [η] of 1.23 dl/g, a molecular weight (Mw) of $3.4 \times 10^4$, a molecular weight distribution (Mw/Mn) of 2.2 and a melting point of 116.8° C. was produced at a rate of $1.3 \times 10^7$ g per one hour per 1 mol of the titanium compound.

EXAMPLE 6

Polymerization was carried out in the same manner as in Example 2 except that triisobutylaluminum was changed to trimethylaluminum of the same molar amount. The temperature in the reactor increased by 0.4° C. by the initial heat generation in this polymerization.

As a result of polymerization, an ethylene-hexene-1 copolymer having an SCB of 9.6, a [η] of 2.13 dl/g, a molecular weight (Mw) of $16.8 \times 10^4$, a molecular weight distribution (Mw/Mn) of 8.3 and a melting point of 119.9° C. was produced at a rate of $7.7 \times 10^6$ g per one hour per 1 mol of the titanium compound.

EXAMPLE 7

Polymerization was conducted in the same manner as in Example 2 except that triphenylcarboniumtetrakis(pentafluorophenyl)borate was changed to [dimethylanilinium] [tetrakis(pentafluorophenyl)borate] of the same molar amount. The temperature raise in the reactor by the initial heat generation in this polymerization was not observed.

As a result of polymerization, an ethylene-hexene-1 copolymer having an SCB of 18.6, and a melting point of 114.1° C. was produced at a rate of $1.9 \times 10^6$ g per one hour per 1 mol of the titanium compound.

EXAMPLE 8

An autoclave having an inner volume of 1 liter equipped with a stirrer as a reactor was dried under vacuum and purged with argon, then, 300 ml of toluene as a solvent was charged into this, and the reactor was heated up to 40° C. After the heating, propylene was fed while controlling the propylene pressure at 4 kg/cm², and after the system was stabilized, 1.25 mmol of triisobutylaluminum was added, subsequently, 5.0 μmol of [dimethyl(3-tert-butyl-2-methoxy-5-methylphenyl)silyl(tetramethylcyclopentadienyl)]titanium dichloride was added, then, 15.0 μm of triphenylcarbeniumtetrakis(pentafluorophenyl)borate was added. Polymerization was carried out for 60 minutes while controlling the temperature at 40° C. The temperature in the reactor increased by 5.2° C. by the initial heat generation in this polymerization.

As a result of polymerization, a propylene homopolymer having a molecular weight (Mw) of $1.04 \times 10^6$, a molecular weight distribution (Mw/Mn) of 2.2, a meso triad of 0.283 and a raceme triad of 0.162 was produced at a rate of $1.6 \times 10^6$ g per one hour per 1 mol of the titanium compound.

EXAMPLE 9

A stirring rod was placed into an autoclave having an inner volume of 0.1 liter, then, the autoclave was dried under vacuum and purged with argon, then, 25 ml of tolueneas a solvent was charged into this, PMAO-S manufactured by Tosoh-Akzo Company, Ltd., was charged in an amount of 6.0 mmol in terms of Al, subsequently, 6.0 μmol of [dimethyl(3-tert-butyl-2-methoxy-5-methylphenyl)silyl(tetramethylcyclopentadienyl)]titanium dichloride was added. Into this was introduced 3.24 g of 1, 3-butadiene, and polymerization was carried out for 60 minutes while controlling the temperature at 25° C.

As a result of polymerization, a 1, 3-butadiene homopolymer having a molecular weight (Mw) of $4.6 \times 10^5$, and a molecular weight distribution (Mw/Mn) of 2.8(ratio of bonding mode of double bond parts in a polymer chain, [1, 4-cis]:[1, 4-trans]:[1, 2-]=0.830:0.070:0.100) was produced at a rate of $4.0 \times 10^4$ g per one hour per 1 mol of the titanium compound.

EXAMPLE 10

An autoclave having an inner volume of 1 liter equipped with a stirrer as a reactor was dried under vacuum and purged with argon, then, 300 ml of toluene as a solvent and 1.0 ml of 5-hexene-1-ol as a comonomer were charged into this, and the reactor was heated up to 40° C. After the heating, 20 mmol of triethylaluminum was added, ethylene was fed while controlling the ethylene pressure at 6 kg/cm², and the mixture was stirred continuously for 15 minutes. After the system was stabilized, 5.0 μmol of [dimethyl(3-tert-butyl-2-methoxy-5-methylphenyl)silyl(tetramethylcyclopentadienyl)]titanium dichloride was added, then, 15.0 μm of triphenylcarbeniumtetrakis(pentafluorophenyl)borate was added. Polymerization was carried out for 60 minutes while controlling the temperature at 40° C. The temperature raise in the reactor by the initial heat generation in this polymerization was not observed.

As a result of polymerization, an ethylene-hexene-1-ol copolymer having a terminal alcohol content of 0.68 wt % and an [η] of 4.96 dl/g was produced at a rate of $1.2 \times 10^5$ g per one hour per 1 mol of the titanium compound.

EXAMPLE 11

An autoclave having an inner volume of 1 liter equipped with a stirrer as a reactor was dried under vacuum and purged with argon, then, 300 ml of toluene as a solvent and 15 ml of vinylcyclohexane as an α-olefin were charged into this, and the reaction vessel was heated up to 60° C. After the heating, ethylene was fed while controlling the ethylene pressure at 6 kg/cm², after the system was stabilized, 0.75 mmol of triisobutylaluminum and 1.5 μmol of [dimethyl(3-tert-butyl-2-methoxy-5-methylphenyl)silyl(tetramethylcyclopentadienyl)]titanium dichloride were added, then, 4.5 μmol of triphenylcarbeniumtetrakis(pentafluorophenyl)borate was added. Polymerization was conducted for 60 minutes while controlling the temperature at 60° C. The temperature raise in the reactor by the initial heat generation in this polymerization was not observed.

As a result of polymerization, an ethylene-vinylcyclohexane copolymer having a content of a vinylcyclohexane unit of 4.1 wt %, an [η] of 2.27 dl/g was produced at a rate of $1.9 \times 10^6$ g per one hour per 1 mol of the titanium compound.

As described in detail above, according to the present invention, a transition metal compound useful for preparing a catalyst for addition polymerization having a catalytic activity which suppresses heat generation at the beginning of polymerization and can be industrially carried out, such a catalyst for addition polymerization, and a process for producing an addition polymer with the catalyst, are provided.

What is claimed is:

1. A transition metal compound represented by the general formula (3):

(3)

wherein M represents a titanium atom, zirconium atom or hafnium atom in the +3 oxidation state; $Cp^1$ represents a group having a cyclopentadiene-containing anion skeleton; J represents an atom of XIV group in the periodic table of element; each of $R^2$ and $R^3$ independently represents a hydrogen atom, halogen atom, alkyl group, aralkyl group, aryl group, substituted silyl group, alkoxy group, aralkyloxy group, aryloxy group or di-substituted amino group, and a plurality of $R^2$ s may bond mutually to form a ring; m represents an integer of from 0 to 4; E represents an oxygen atom or sulfur atom; $R^1$ represents an alkyl group, aralkyl group, aryl group or substituted silyl group; each of two Xs independently represents a hydrogen atom, halogen atom, alkyl group, aralkyl group, aryl group, substituted silyl group, alkoxy group, aralkyloxy group, aryloxy group or di-substituted amino group, and two Xs may bond mutually to form a ring; D represents a neutral ligand coordinated on M; and n represents an integer of from 0 to 2.

2. The transition metal compound according to claim 1, wherein E represents an oxygen atom.

3. The transition metal compound according to claim 1, wherein M represents a titanium atom.

4. The transition metal compound according to claim 1, wherein $R^1$ represents a methyl group.

5. A transition metal compound represented by the general formula (3):

(3)

wherein M represents a titanium atom, zirconium atom or hafnium atom in the +3 oxidation state; $Cp^1$ represents a group selected from the group consisting of a cyclopentadienyl group, substituted cyclopentadienyl group, idenyl group, substituted idenyl group, fluorenyl group and substituted fluorenyl group; J represents an atom of XIV group in the periodic table of element; each of $R^2$ and $R^3$ independently represents a hydrogen atom, halogen atom, alkyl group, aralkyl group, aryl group, substituted silyl group, alkoxy group, aralkyloxy group, aryloxy group or di-substituted amino group, and a plurality of R2 s may bond mutually to form a ring; m represents an integer of from 0 to 4; E represents an oxygen atom or sulfur atom; $R^1$ represents an alkyl group, aralkyl group, aryl group or substituted silyl group; each of two Xs independently represents a hydrogen atom, halogen atom, alkyl group, aralkyl group, aryl group, substituted silyl group, alkoxy group, aralkyloxy group, aryloxy group or di-substituted amino group, and two Xs may bond mutually to form a ring; D represents a neutral ligand coordinated on M; and n represents an integer of from 0 to 2.

* * * * *